(12) United States Patent
Nan et al.

(10) Patent No.: US 10,414,713 B2
(45) Date of Patent: Sep. 17, 2019

(54) FATTY ACID COMPOUND, PREPARATION METHOD THEREFOR AND USE THEREFOR

(71) Applicant: SHANGHAI INSTITUTE OF MATERIA MEDICA, CHINESE ACADEMY OF SCIENCES, Pudong, Shanghai (CN)

(72) Inventors: Fajun Nan, Shanghai (CN); Jia Li, Shanghai (CN); Jingya Li, Shanghai (CN); Mei Zhang, Shanghai (CN); Zhifu Xie, Shanghai (CN); Jingtao Wang, Shanghai (CN); Dongdong Guo, Shanghai (CN)

(73) Assignee: SHANGHAI INSTITUTE OF MATERIA MEDICA, CHINESE ACADEMY OF SCIENCES, Pudong, Shanghai (CN)

( * ) Notice: Subject to any disclaimer, the term of this patent is extended or adjusted under 35 U.S.C. 154(b) by 0 days.

(21) Appl. No.: 16/075,528

(22) PCT Filed: Feb. 20, 2017

(86) PCT No.: PCT/CN2017/074039
§ 371 (c)(1),
(2) Date: Aug. 3, 2018

(87) PCT Pub. No.: WO2017/143946
PCT Pub. Date: Aug. 31, 2017

(65) Prior Publication Data
US 2019/0039989 A1    Feb. 7, 2019

(30) Foreign Application Priority Data
Feb. 25, 2016 (CN) .......................... 2016 1 0105067

(51) Int. Cl.
| | | |
|---|---|---|
| *A61K 31/194* | (2006.01) | |
| *C07C 55/28* | (2006.01) | |
| *C07C 57/13* | (2006.01) | |
| *C07C 57/42* | (2006.01) | |
| *C07C 57/26* | (2006.01) | |
| *C07C 61/16* | (2006.01) | |
| *C07C 61/20* | (2006.01) | |
| *C07C 61/22* | (2006.01) | |
| *C07C 61/35* | (2006.01) | |

(52) U.S. Cl.
CPC ............ *C07C 61/35* (2013.01); *A61K 31/194* (2013.01); *C07C 55/28* (2013.01); *C07C 57/13* (2013.01); *C07C 57/26* (2013.01); *C07C 57/42* (2013.01); *C07C 61/16* (2013.01); *C07C 61/20* (2013.01); *C07C 61/22* (2013.01); *C07C 2601/08* (2017.05); *C07C 2601/16* (2017.05); *Y02P 20/55* (2015.11)

(58) Field of Classification Search
CPC ......... C07C 61/35; C07C 55/28; C07C 57/13; C07C 57/26; C07C 57/42; C07C 61/16; C07C 61/20; C07C 61/22; A61K 31/194
USPC ........................................................ 514/560
See application file for complete search history.

(56) References Cited

U.S. PATENT DOCUMENTS

| | | | | |
|---|---|---|---|---|
| 3,773,946 | A | * 11/1973 | Creger | ..................... C07C 55/02 514/547 |
| 3,930,024 | A | * 12/1975 | Creger | ..................... C07F 9/091 514/738 |
| 4,689,344 | A | 8/1987 | Bar-Tana | |
| 4,711,896 | A | 12/1987 | Bar-Tana et al. | |
| 2004/0198814 | A1* | 10/2004 | Dasseux | ................. C07C 49/17 514/526 |
| 2012/0071528 | A1* | 3/2012 | Khanna | ................... C07C 31/27 514/381 |

FOREIGN PATENT DOCUMENTS

| | | | |
|---|---|---|---|
| WO | 9611901 | 4/1996 | |
| WO | WO-9830530 A1 * | 7/1998 | ............. C07C 55/02 |

OTHER PUBLICATIONS

Yi; Appl Microbiol Biotechnol 1989, 30, 327-331. (Year: 1989).*
Voss; WO1996011901; Unverified Machine Translation from EPO, 23 pages. First published in German on Apr. 25, 1996. (Year: 1996).*
Bar-Tana; Journal of Medicinal Chemistry 1989, 32, 2072-2084. (Year: 1989).*
Oniciu; J. Med. Chem. 2006, 49, 1, 334-348. (Year: 2006).*
Ramesh; Appl Biochem Biotechnol 2016, 178, 810-830. (Year: 2016).*
International Search Report of International Application No. PCT/CN2017/074039 dated May 24, 2017.
CAS. "RN 71042-01-8 et al." STN Registry, Jun. 5, 2009.

* cited by examiner

*Primary Examiner* — Daniel R Carcanague
(74) *Attorney, Agent, or Firm* — Ping Wang; Morris, Manning & Martin, LLP

(57) ABSTRACT

The present invention relates to a class of fatty acid compounds, a preparation method thereof and use thereof. The fatty acid compounds have the structure of the formula I, which has the ability to activate APMK and inhibit the glucose output in mouse primary hepatocytes. The fatty acid compounds can be used in preparing a medicament for the treatment of obesity or diabetes.

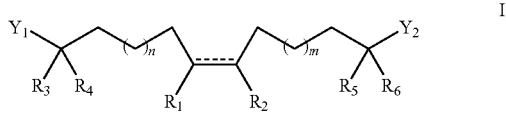

9 Claims, 2 Drawing Sheets

FATTY ACID COMPOUND, PREPARATION METHOD THEREFOR AND USE THEREFOR

TECHNICAL FIELD

The present invention belongs to the field of medicinal chemistry, and relates to a class of fatty acid compounds or pharmaceutically acceptable salts thereof, preparation methods for the same and pharmaceutical compositions comprising these compounds. Such compounds have the ability of activating AMPK in human HepG2 hepatoma cells and inhibiting the glucose output capacity of primary hepatocytes in C57bl/6j mice, which can be used to prepare drugs for treating obesity and diabetes.

BACKGROUND

Diabetes mellitus is a group of metabolic disorders caused by islet dysfunction, insulin resistance etc. A variety of pathogenic factors, such as genetic factors, immune dysfunction, mental factors, can cause diabetes. According to the statistics of the World Health Organization in 2011, 366 million people had diabetes worldwide. Diabetes has become the third largest disease, following cardio-cerebrovascular diseases and malignant tumors. China has been the world's biggest diabetes country with a prevalence rate of 9.7%, which is higher than the world's average. With 92.4 million diabetics in total, China is ranking the top in the world.

Now, there are many drugs for the treatment of type II diabetes, including metformin, sulfonylureas, DPP-4 inhibitors, PPARγ agonists, α-glucosidase inhibitors, insulin and GLP-1 analogues, etc. However, the present drugs have some defects, such as insignificant curative effect, and short acting time. Some drugs even have side effects like hypoglycemia, weight gain, edema, fracture, lactic acidosis and gastrointestinal discomfort etc.

Adenosine monophosphate activated protein kinase (AMPK) plays a leading role in the glucolipid metabolism in vivo. It is an energy meter and main metabolic switch that senses and decodes intracellular changes in energy status. AMPK activation can significantly treat the metabolic disorders of type II diabetes, and improve insulin sensitivity in vivo. It has been confirmed as a new target for the treatment of type II diabetes. Clinical drugs with hypoglycemic and lipid-lowering effects, like metformin, TZDs and berberine, have been proved to be able to activate AMPK at the cellular level, which paved a rout for AMPK as a new anti-diabetic drug target.

A class of fatty acid compounds have been designed and synthesized. These compounds have the ability to activate AMPK at the cellular level and inhibit mouse primary hepatocyte glucose output. Some of these compounds exhibit excellent AMPK activation effects, and could significantly stimulate the phosphorylation of AMPK and ACC in a concentration-dependent manner at the cellular level. Most of the compounds had the significantly effect of reducing glucose output. Such compounds have tremendous development potentials as therapeutic drugs for diabetes.

SUMMARY OF THE INVENTION

A class of fatty acid compounds was designed and synthesized. These compounds were found to be able to activate AMPK and reduce primary mouse hepatocyte glucose output. The compounds represented by Formula I-IV have the ability to activate AMPK. These compounds can significantly promote the phosphorylation of AMPK and ACC in HepG2 cells in a dose-dependent manner and have the significantly effect of inhibiting the glucose output.

Therefore, one object of the present invention is to provide a novel class of fatty acid compounds having the ability to activate AMPK or pharmaceutically acceptable salts thereof.

Another object of the present invention is to provide a method for preparing such fatty acid compounds having the ability to activate AMPK or a pharmaceutically acceptable salt thereof.

Another object of the present invention is to provide a pharmaceutical composition including a fatty acid compound having the ability to activate AMPK, which comprises a therapeutically effective amount of the said fatty acid compound in the present invention or a pharmaceutically acceptable salt thereof as an active ingredient and a pharmaceutically acceptable adjuvant.

A further object of the present invention is to provide a use of the fatty acid compounds or pharmaceutically acceptable salts thereof and pharmaceutical compositions thereof in the preparation of a medicament as an AMPK activator, particularly, in the preparation of a medicament for the treatment of obesity or diabetes.

The present invention provides a fatty acid compound represented by following formula I:

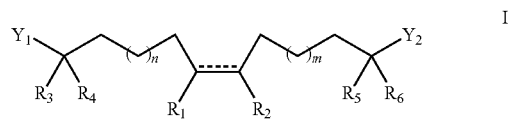

wherein, $R_1$, $R_2$, $R_3$, $R_4$, $R_5$, and $R_6$ are each independently H, C1~C4 alkyl, C1~C4 alkenyl, C1~C4 alkynyl, C3~C7 cycloalkyl, C3~C7 cycloalkenyl, phenyl or benzyl, preferably, $R_1$, $R_2$, $R_3$, $R_4$, $R_5$, and $R_6$ are each independently H, C1~C3 alkyl, C3~C6 cycloalkyl, C3~C6 cycloalkenyl, or phenyl, alternatively, $R_1$ and $R_2$ together with their adjacent carbon atoms form a C3-C7 cycloalkyl group, or together with their adjacent carbon atoms form a C3-C7 cycloalkenyl group;

alternatively, $R_3$ and $R_4$ together with their adjacent carbon atoms form a C3~C7 cycloalkyl group, or together with their adjacent carbon atoms form a C3~C7 cycloalkenyl group;

alternatively, $R_5$ and $R_6$ together with their adjacent carbon atoms form a C3~C7 cycloalkyl group, or together with their adjacent carbon atoms form a C3~C7 cycloalkenyl group, m, n are each independently 1, 2, 3, 4, 5 or 6, preferably 2, 3, 4 or 5, $Y_1$ and $Y_2$ are each independently —OH, —COOH, —COOR$_7$, —SO$_3$H, —SO$_2$NHR, —PO(OH)OEt, —CONHCN,

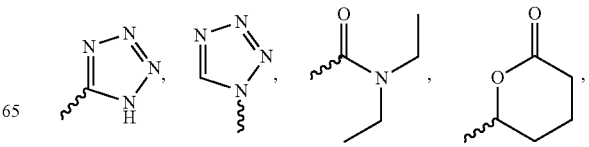

-continued

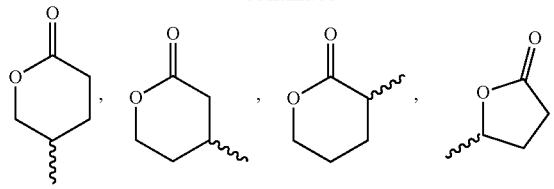

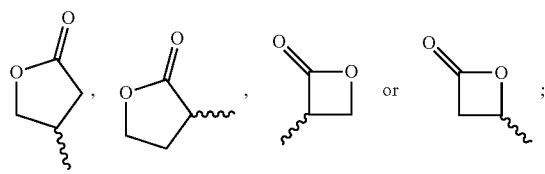

wherein, $R_7$ is methyl or ethyl, R is methyl or ethyl; preferably, $Y_1$ and $Y_2$ are each independently —COOH, ═ represents a double bond or a single bond, the double bond is either cis or trans.

In the present invention, the said alkyl group includes a linear or branched alkyl group, and the said alkenyl group includes a linear or branched alkenyl group.

In a preferred embodiment, the fatty acid compound of the present invention is represented by the following formula II:

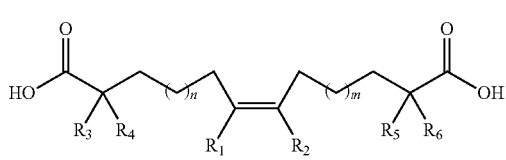

wherein $R_1$, $R_2$, $R_3$, $R_4$, $R_5$ and $R_6$ are each independently H, C1~C4 alkyl, C1~C4 alkenyl, C1~C4 alkynyl, C3~C7 cycloalkyl, C3~C7 cycloalkenyl, phenyl or benzyl; preferably, $R_1$, $R_2$, $R_3$, $R_4$, $R_5$, $R_6$ are each independently H, C1~C3 alkyl, C3~C6 cycloalkyl, C3~C6 cycloalkenyl or phenyl; more preferably, $R_1$ and $R_2$ are H, $R_3$, $R_4$, $R_5$, $R_6$ are each independently H, C1~C3 alkyl or phenyl.

alternatively, $R_5$ and $R_6$ together with their adjacent carbon atoms form a C3~C7 cycloalkyl group, or together with their adjacent carbon atom form a C3~C7 cycloalkenyl group, alternatively, $R_3$ and $R_4$ together with their adjacent carbon atoms form a C3~C7 cycloalkyl group, or together with their adjacent carbon atoms form a C3~C7 cycloalkenyl group;

m, n are each independently 1, 2, 3, 4, 5 or 6, preferably 2, 3, 4 or 5, the double bond is either cis or trans.

In another preferred embodiment, the fatty acid compound of the present invention is represented by the following formula III:

wherein, $R_3$, $R_4$, $R_5$, $R_6$ are each independently H, C1~C4 alkyl, C1~C4 alkenyl, C1~C4 alkynyl, C3~C7 cycloalkyl, C3~C7 cycloalkenyl, phenyl or benzyl, preferably, $R_3$, $R_4$, $R_5$, $R_6$ are each independently H, C1~C3 alkyl, C3~C6 cycloalkyl, C3~C6 cycloalkenyl or phenyl, alternatively, $R_5$ and $R_6$ together with their adjacent carbon atoms form a C3~C7 cycloalkyl group, or together with their adjacent carbon atoms form a C3~C7 cycloalkenyl group, alternatively, $R_3$ and $R_4$ together with their adjacent carbon atoms form a C3~C7 cycloalkyl group, or together with their adjacent carbon atoms form a C3~C7 cycloalkenyl group, m, n are each independently 1, 2, 3, 4, 5 or 6, preferably 2, 3, 4 or 5.

In another preferred embodiment, the fatty acid compound of the present invention is represented by the following formula IV:

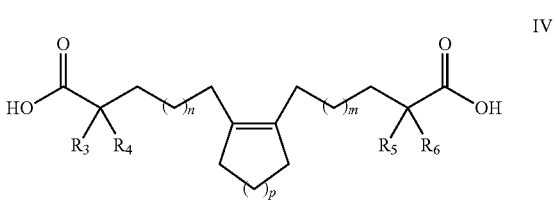

wherein, $R_3$, $R_4$, $R_5$, $R_6$ are each independently H, C1~C4 alkyl, C1~C4 alkenyl, C1~C4 alkynyl, C3~C7 cycloalkyl, C3~C7 cycloalkenyl, phenyl or benzyl, preferably, $R_3$, $R_4$, $R_5$, $R_6$ are each independently H, C1~C3 alkyl, C3~C6 cycloalkyl, C3~C6 cycloalkenyl or phenyl;

alternatively, $R_5$ and $R_6$ together with their adjacent carbon atoms form a C3~C7 cycloalkyl group, or together with their adjacent carbon atoms form a C3~C7 cycloalkenyl group, alternatively, $R_3$ and $R_4$ together with their adjacent carbon atoms form a C3~C7 cycloalkyl group, or together with their adjacent carbon atoms form a C3~C7 cycloalkenyl group.

m, n are each independently 1, 2, 3, 4, 5 or 6, preferably 2, 3, 4 or 5, p is 1, 2 or 3, preferably 2.

The said fatty acid compound having the ability to activate AMPK is most preferably selected from the following compound:

Compound 1

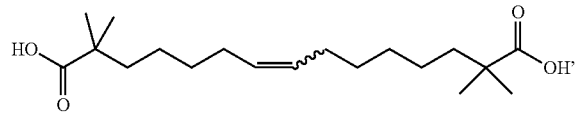

Compound 2

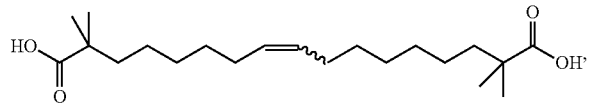

-continued
Compound 3
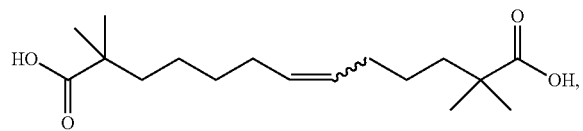
Compound 4
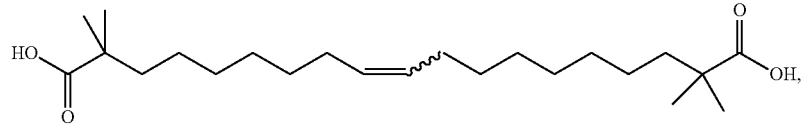
Compound 5
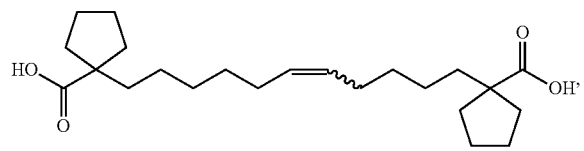
Compound 6
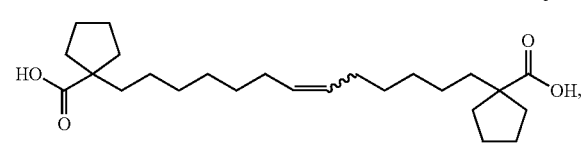
Compound 7
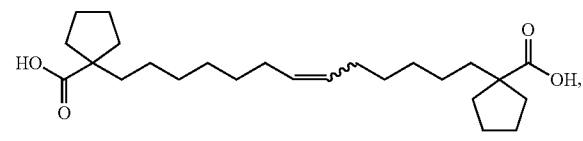
Compound 8
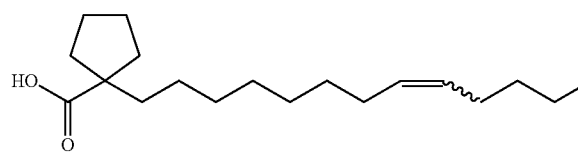
Compound 9
Compound 10
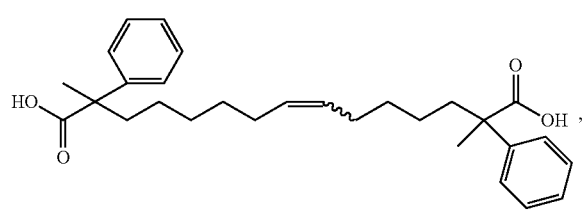
Compound 11
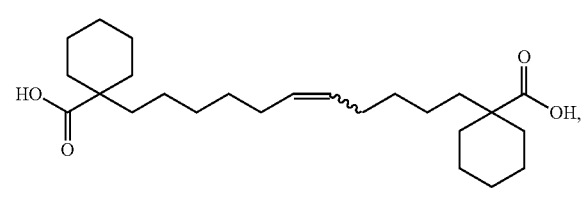
Compound 12
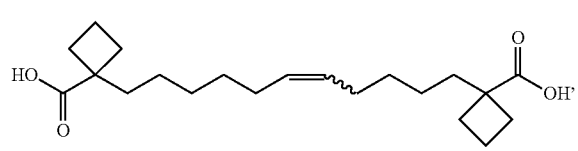
Compound 13
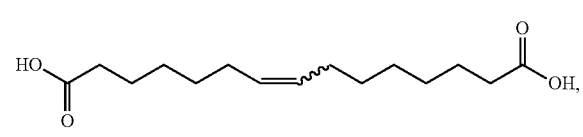
Compound 14
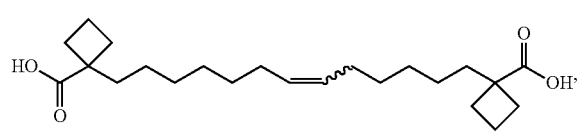
Compound 15
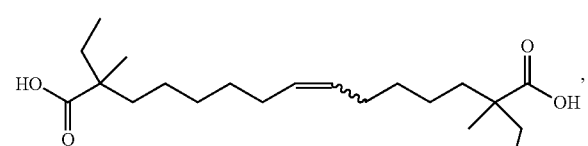
Compound 16
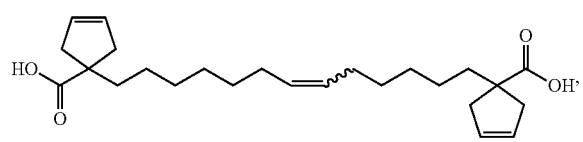
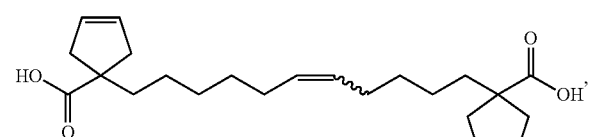

-continued
Compound 17
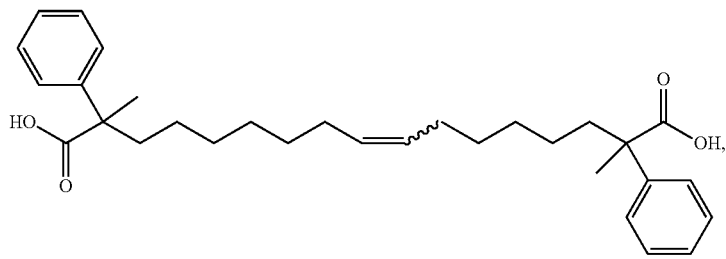
Compound 18
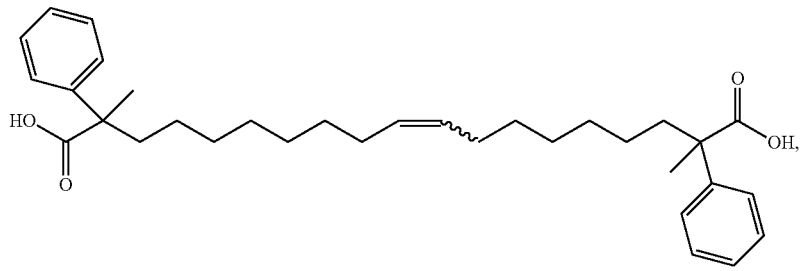
Compound 19
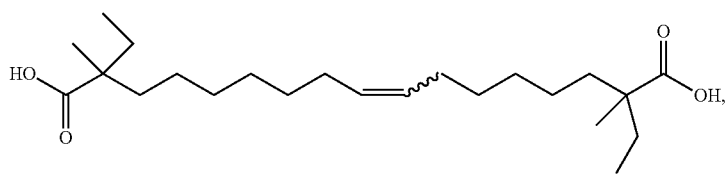
Compound 20
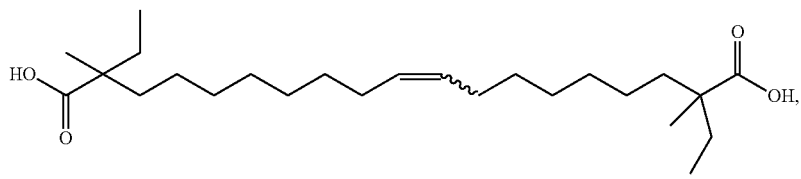
Compound 21
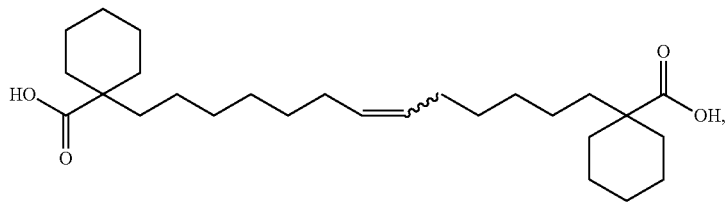
Compound 22
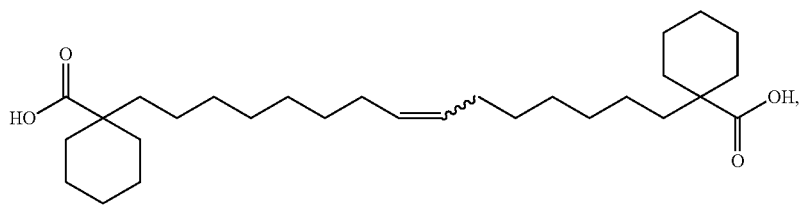
Compound 23
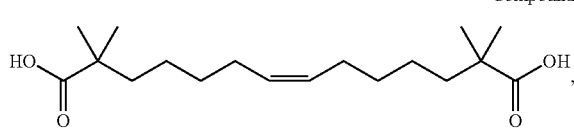
Compound 24
Compound 25
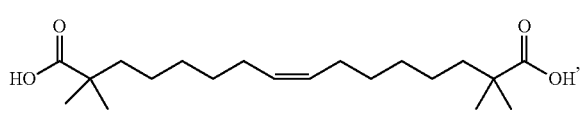
Compound 26
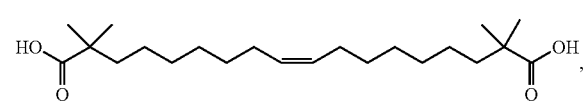

-continued

Compound 27

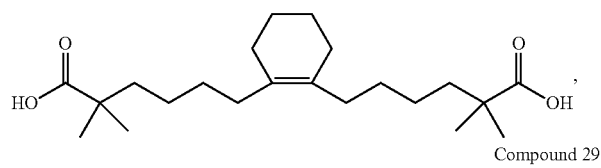

Compound 28

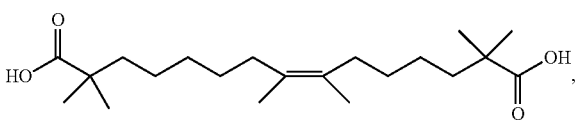

Compound 29

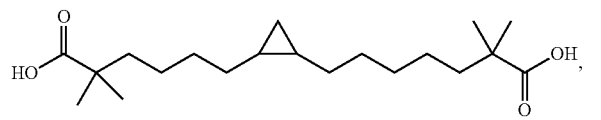

Compound 30

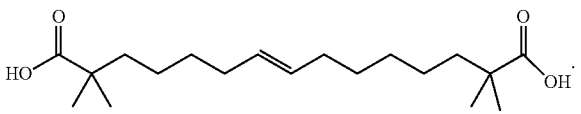

The said compound represented by the formula I-IV or a pharmaceutically acceptable salt thereof can be prepared through conventional reactions in organic synthesis. The compound of the formula I-III can be synthesized by the following route.

Route 1:

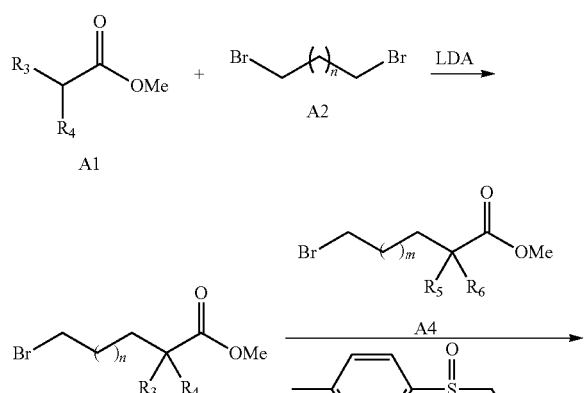

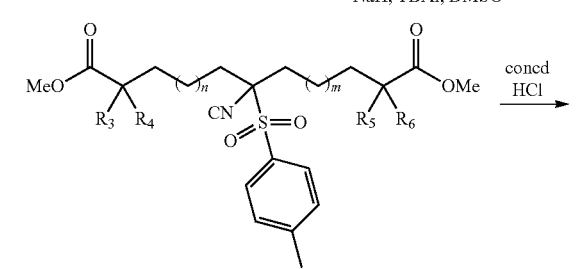

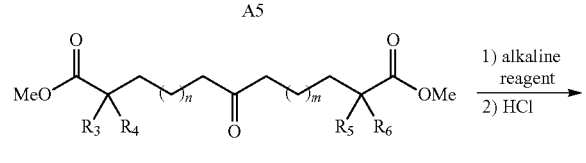

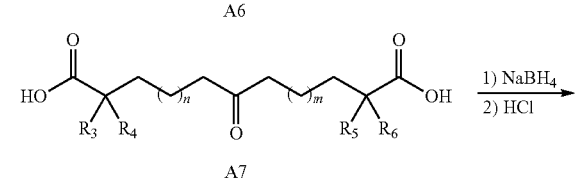

-continued

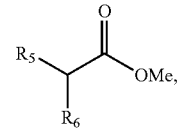

(1) reacting substituted ethyl acetate A1 with dibromoalkane A2 through a condensation reaction in the presence of lithium diisopropylamide (LDA) and an organic solvent to obtain intermediate A3; under the same conditions, replacing A1 with and reacting with A2 to give A4; wherein, the organic solvent is preferably tetrahydrofuran (THF);

(2) reacting equivalent A3 and A4 with tosylmethyl isocyanide in the presence of NaH, tetrabutylammonium iodide (TBAI), and dimethyl sulfoxide (DMSO) to obtain compound A5;

(3) reacting A5 with concentrated hydrochloric acid to remove hydrocyanic acid and p-toluenesulfonic acid to obtain A6; wherein, the reaction can be carried out in an organic solvent, the organic solvent is preferably dichloromethane (DCM);

(4) under alkaline conditions, conducting A6 a hydrolysis reaction and acidulating by dilute hydrochloric acid to obtain A7; wherein, the said alkaline reagent is preferably KOH; and the said hydrolysis reaction which removes the ester group is preferably carried out in the presence of an organic solvent such as ethanol;

(5) further reducing A7 with sodium borohydride to obtain A8;

(6) refluxing a toluene solution including A8 and the catalyst p-toluenesulfonic acid to obtain a compound A9 or A10.

Route 2:

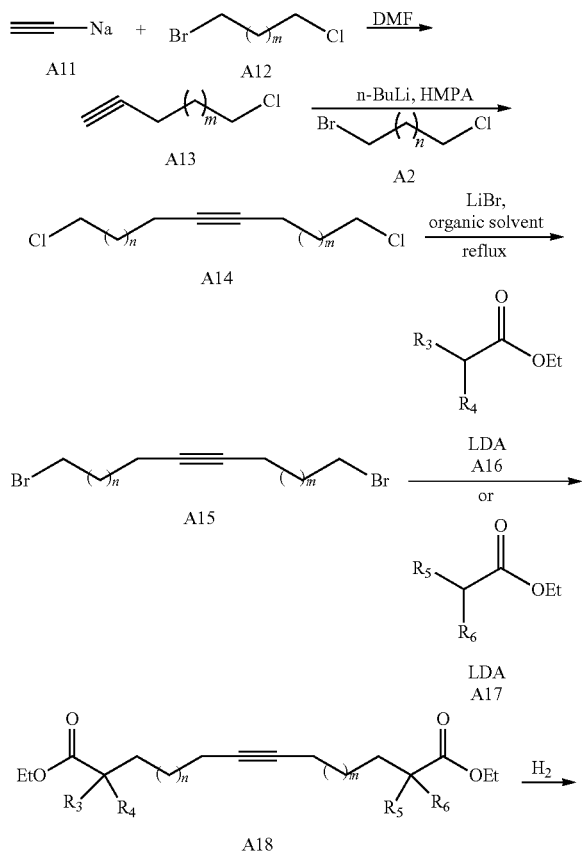

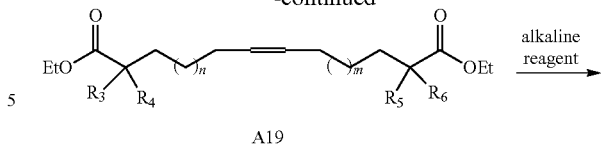

(1) reacting sodium acetylide A11 with bromo A12 in DMF to obtain intermediate A13;

(2) condensing alkynyl compound A13 and brominated compound A2 in the presence of n-butyl lithium and hexamethylphosphoric triamide (HMPA) to give intermediate A14;

(3) refluxing intermediate A14 with lithium bromide in an organic solvent to give intermediate A15; wherein, the said organic solvent is preferably acetone;

(4) condensing A15 with A16 or A17 in the presence of lithium diisopropylamide (LDA) to obtain intermediate A18;

(5) conducting A18 a hydrogenation reaction to obtain intermediate A19;

(6) under alkaline conditions, conducting A19 a hydrolysis reaction and acidulating by dilute hydrochloric acid to obtain A20; wherein, the said alkaline reagent is preferably KOH; and the said hydrolysis reaction which removes the ester group is preferably carried out in the presence of an organic solvent such as ethanol.

Intermediate A15 of Route 2 can also be prepared through route 3.

Route 3:

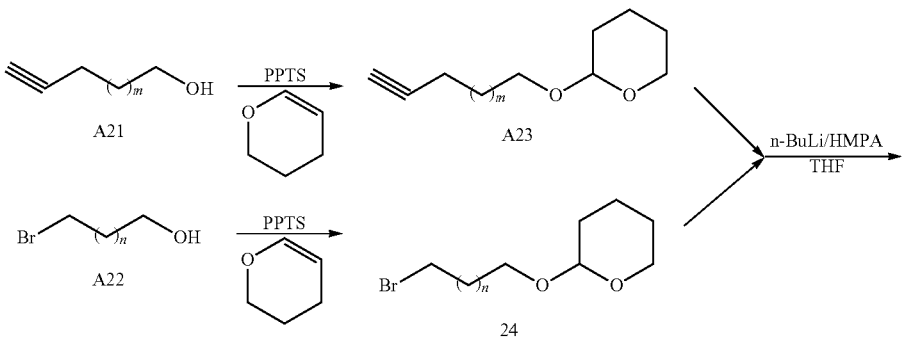

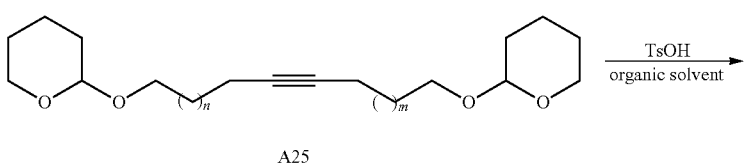

(1) reacting 1-alkynyl-alcohol compound A21 in the presence of pyridine p-toluenesulfonate (PPTS) and 2-tetrahydropyran (THP) to give intermediate A23; reacting 1-hydroxy-bromo compound A22 in the presence of pyridine p-toluenesulfonate and 2-tetrahydropyran (THP) to obtained intermediate A24;

(2) condensing A23 with A24 in the presence of n-butyl lithium and HMPA to give intermediate A25;

(3) deprotection of A25 in the presence of p-toluenesulfonic acid (TsOH) and an organic solvent to obtain intermediate A26; wherein, the said organic solvent is preferably methanol;

(4) reacting A26 with carbon tetrabromide and triphenylphosphine (PPh$_3$) to give the intermediate A15.

In routes 1-3: the definitions of $R_3$, $R_4$, $R_5$, $R_6$, n and m in the reaction formulas are the same as described above.

The compound represented by the formula II is synthesized by the following route 4, Route 4:

(1) reacting intermediate A18 with bis(pinacolato)diboron catalyzed by tetrakis(triphenylphosphine)platinum to form intermediate A26;

(2) conducting A26 a coupling reaction with iodide $R_1$I or $R_2$I to give intermediate A27;

(3) under alkaline conditions, conducting A27 a hydrolysis reaction and acidulating by dilute hydrochloric acid to obtain the compound represented by the formula II.

wherein, the definitions of $R_3$, $R_4$, $R_5$, $R_6$, m and n are the same as described above.

The compound represented by formula III is prepared through the following route 5.

Route 5:

addition of iodine methane to intermediate A20 with ethyl zinc reagent to give intermediate A28; under alkaline conditions, conducting intermediate A28 a hydrolysis reaction and acidulating by dilute hydrochloric acid to obtain the compound represented by the formula III.

wherein, the definitions of $R_3$, $R_4$, $R_5$, $R_6$, m and n are the same as described above.

The compound represented by the formula IV is prepared by the following route 6.

Route 6:

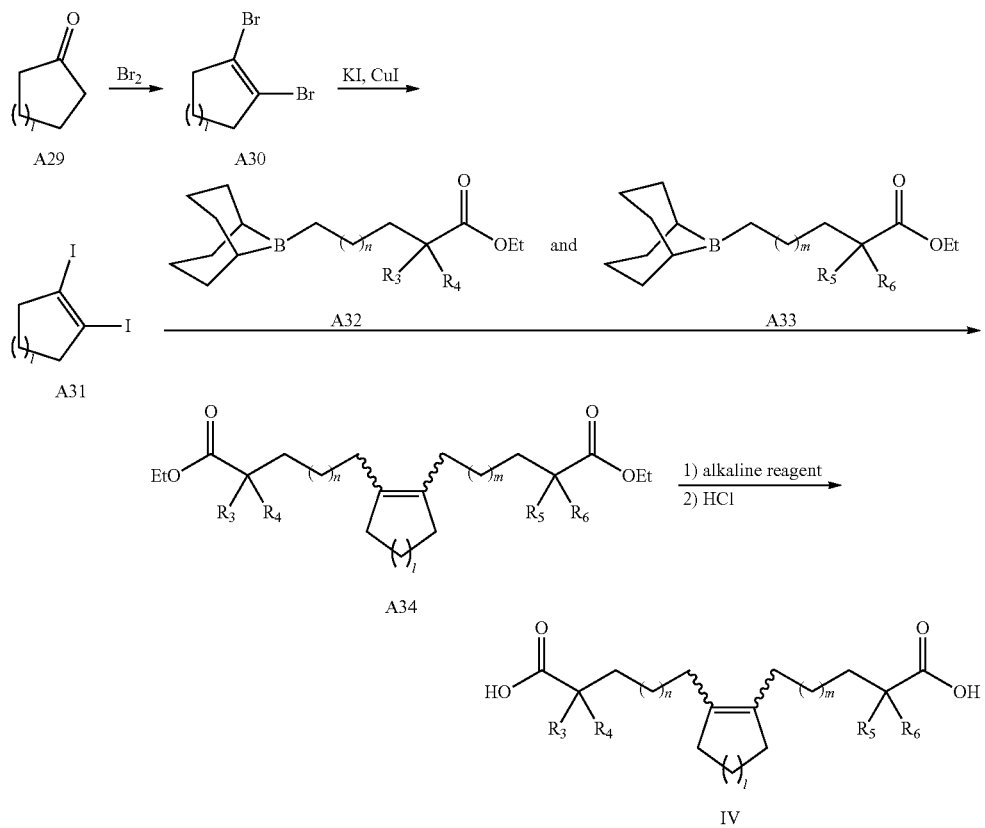

(1) first, converting compound A29 to a bromo olefin intermediate A30;
(2) converting intermediate A30 to intermediate A31 in the presence of potassium iodide and cuprous iodide;
(3) further coupling A31 with boron reagents A32 and A33 to obtain intermediate A34;
(4) under alkaline conditions, conducting A34 a hydrolysis reaction and acidulating by dilute hydrochloric acid to obtain the compound represented by the formula IV; wherein, the said alkaline reagent is preferably KOH; and the said hydrolysis reaction which removes the ester group is preferably carried out in the presence of an organic solvent such as ethanol.

Wherein, the definitions of $R_3$, $R_4$, $R_5$, $R_6$, m, n and p are the same as described above.

The compounds of the present invention having the ability to activate AMPK improve glycolipid metabolism at the cellular and whole animal level. The compounds can be used for the preparation of a medicament for treating obesity or diabetes.

The present invention provides a pharmaceutical composition for treating obesity or diabetes. The pharmaceutical composition comprises a therapeutically effective amount of one or more compounds represented by the formula I, or pharmaceutically acceptable salts thereof as an active ingredient, and pharmaceutically acceptable adjuvants such as dispersing agents, excipients, disintegrating agents, antioxidants, sweeteners, coating agents. The pharmaceutical composition can be prepared according to a conventional preparation method in the pharmaceutical field, and can be made into various conventional dosage forms, including tablets, coated tablets, capsules, powders and so on.

DETAILED DESCRIPTION OF EXEMPLARY EMBODIMENTS

Figure 1:
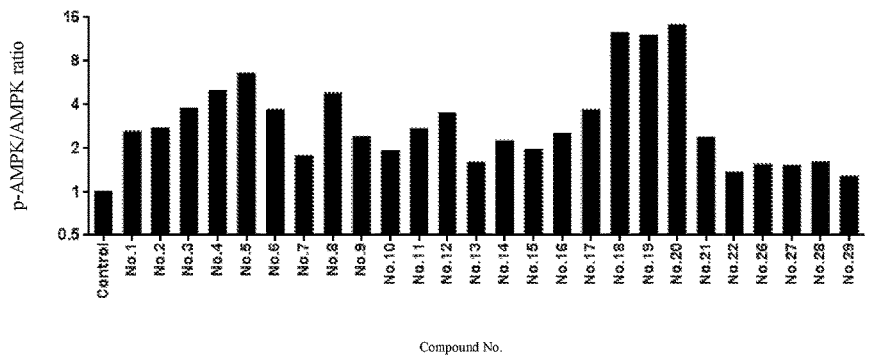
FIG. 1 is a bar graph of the compound promoting phosphorylation of AMPK in human HepG2 liver cancer cells.

The present invention will be further illustrated based on the following examples, but the present invention will not be limited thereto.

Preparation Examples for Compounds

In following preparation examples, NMR was conducted on a Mercury-Vx 300M instrument manufactured by Varian; Mass spectra were obtained using Agilent 1200 Quadrupole LC/MS mass spectrometer. Reagents are mainly provided by Shanghai Chemical Reagent Company. The silica gel plate (model GF 254) for thin layer chromatography (TLC) was manufactured by Huiyou Silica gel Development Co. Ltd., Yantai, Shandong. The compounds were purified by column chromatography with a silica gel of 200-300 mesh, model-zcx-11, manufactured by Qingdao Haiyang Chemical Co. Ltd.

Preparation Example 1: 1-(5-(6-oxo-7-heterospiro[4.8]tridec-8-yl)pentyl)cyclopentanecarboxylic acid (Compound 5)
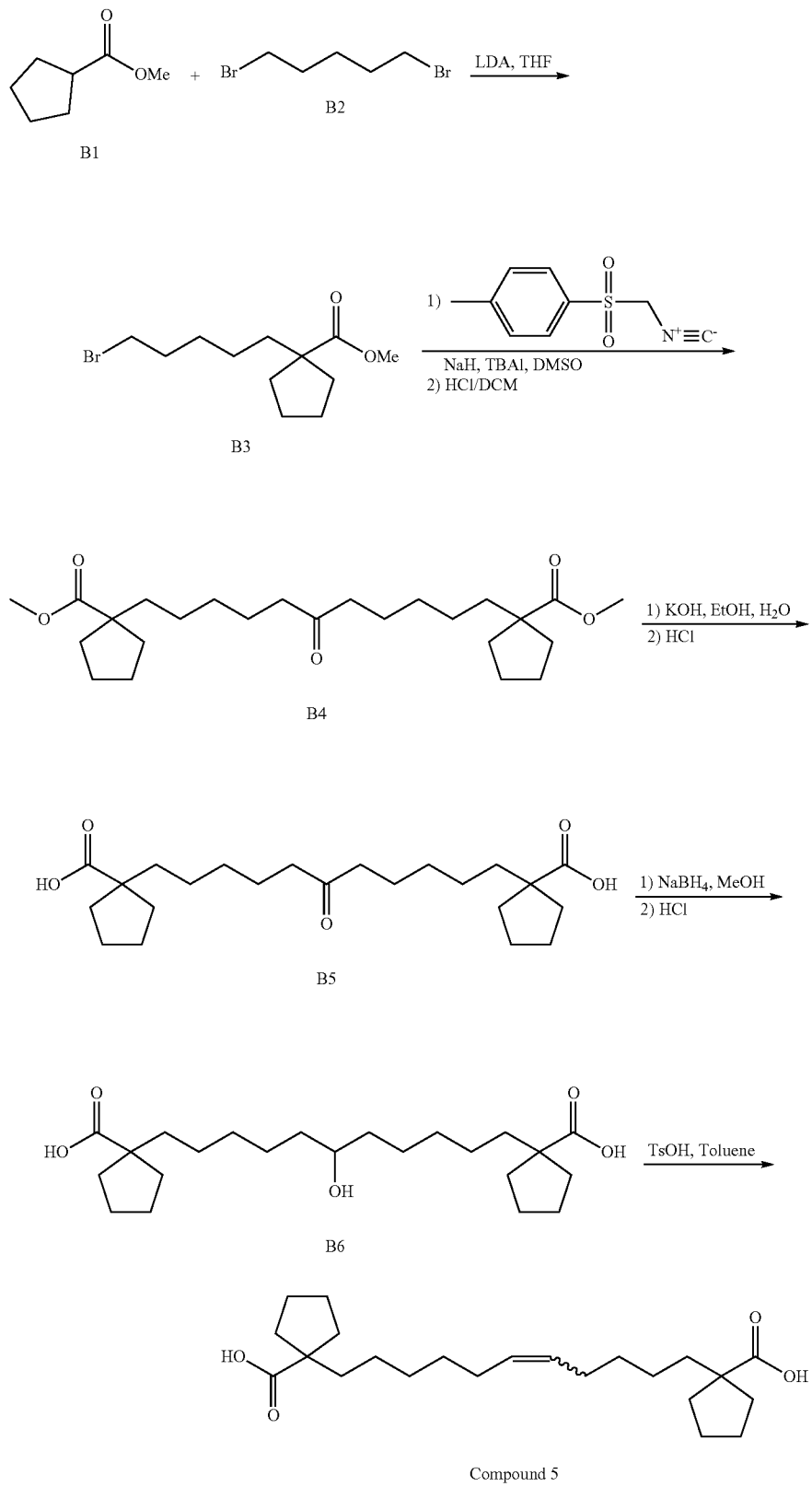

(1) Methyl 1-(5-bromopentyl)cyclopentanecarboxylate (Compound B3)

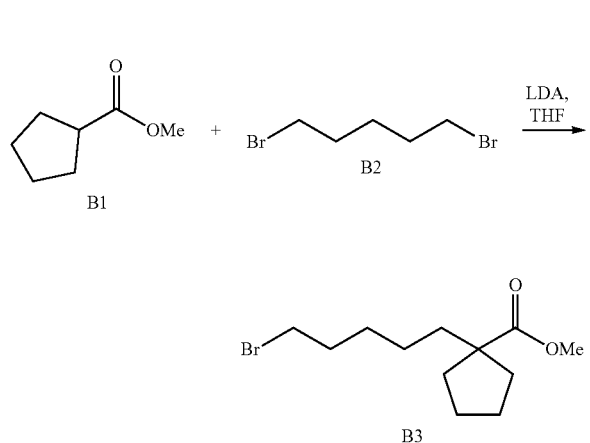

Under the argon gas protection, methyl cyclopentanecarboxylate 1.28 g (10 mmol) and 1,5-dibromopentane 2.49 g (11 mmol) were added to the reaction flask, dissolved in 50 mL of tetrahydrofuran, and cooled to 0° C. LDA (0.467 mmol) was slowly added in a drop wise manner for about 1 hour. After then, the reaction was stirred overnight at room temperature, and monitored by TLC on the next day. The reaction was quenched by the addition of a saturated aqueous solution of ammonium chloride. After the addition, the mixture was extracted three times with EtOAc. The combined organic layers were washed with brine, dried over anhydrous $Na_2SO_4$, concentrated and purified by using column chromatography with PE:EA (v/v)=100:1, to provide 1.7 g of compound B3 as a pale yellow liquid, yield 62%. $^1$H NMR (300 MHz, $CDCl_3$) δ3.63 (s, 3H), 3.36 (t, 2H), 2.05-2.09 (m, 2H), 1.78-1.83 (m, 2H), 1.54-1.60 (m, 6H), 1.35-1.44 (m, 4H), 1.18-1.21 ppm (m, 2H).

(2) 6-carbonyl-undecane-1,11-dicyclopentanecarboxylate (Compound B4)

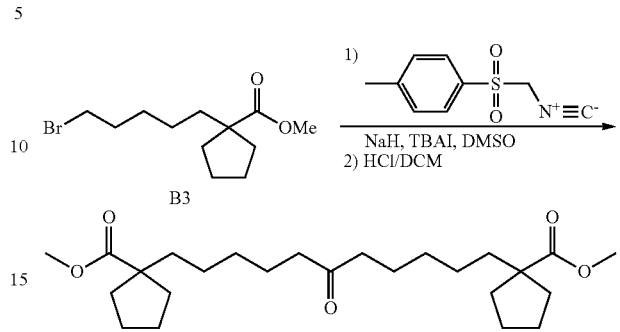

Under the argon gas protection, compound B3 (1.7 g, 6.2 mmol), tosylmethyl isocyanide (0.64 g, 3.1 mmol) and tetrabutylammonium iodide (0.23 g, 0.62 mmol) were dissolved in 10 mL of DMSO. The solution was cooled to 0° C., added sodium hydride (60%) (0.3 g, 7.4 mmol) in portions. After then, the reaction was stirred overnight at room temperature, and monitored by TLC on the next day. The reaction mixture was quenched with water. After then, the mixture was extracted three times with DCM. The combined organic layers were washed with brine, dried over anhydrous $Na_2SO_4$, concentrated and held for use in the next step without purification. The crude product was added 20 mL of DCM, and 4 mL of concentrated hydrochloric acid. The reaction was stirred at room temperature for 1 hour, and diluted with water, extracted with dichloromethane for three times. The organic phase was washed with brine, dried over anhydrous $Na_2SO_4$. The solvent was removed using rotary evaporation. The residue was purified by using column chromatography with PE:EA (v/v)=30:1, to provide 850 mg of compound B4, as a pale yellow liquid, yield 65%. $^1$H NMR (300 MHz, $CDCl_3$) δ3.63 (s, 6H), 2.33 (t, 4H), 2.04-2.09 (m, 4H), 1.52-1.58 (m, 16H), 1.40-1.52 (m, 4H), 1.17-1.23 ppm (m, 8H).

(3) 6-carbonyl-undecane-1,11-dicyclopentanecarboxylic acid (Compound B5)

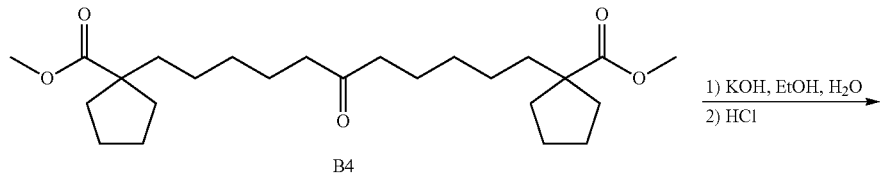

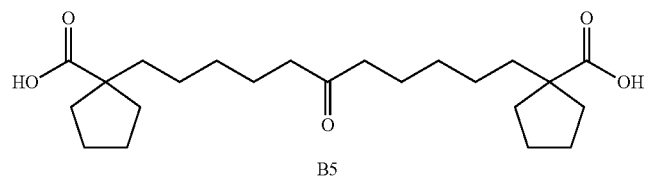

Compound B4 (422 mg, 1 mmol) was dissolved in 10 mL of ethanol and added 2 mL of an aqueous solution of KOH (500 mg, 8.9 mmol). The reaction mixture was refluxed for 3 hours, and monitored by TLC. After the reaction was completed, the mixture was cooled to room temperature, and most of the ethanol was removed by rotary evaporation. The residue was diluted with water and extracted with DCM to remove a small amount of impurities. The mixture was adjusted to acidity by adding 2N HCl, and extracted with DCM for three times. The organic phase was washed with brine, dried over anhydrous $Na_2SO_4$, concentrated to get a 300 mg of crude product which was held for use in the next step without purification.

(4)
6-Hydroxy-undecane-1,11-dicyclopentanecarboxylic acid (Compound B5)

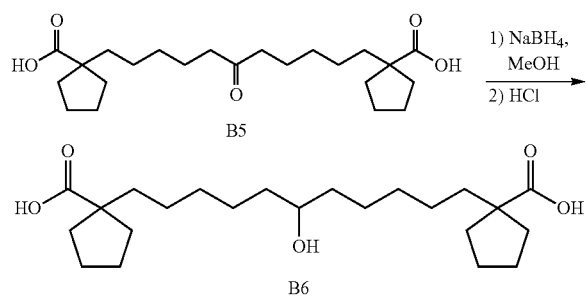

Compound B5 (366 mg, 1 mmol) was dissolved in 10 mL of methanol, cooled to 0° C. The mixture was added sodium borohydride (76 mg, 2 mmol) and stirred for 0.5 h, followed by adding 304 mg of sodium hydride (8 mmol) in portions. After then, the reaction was stirred at room temperature for 1 hour, monitored by TLC. After the reaction was completed, the mixture was diluted with water, was adjusted to acidity by adding 2N HCl. The mixture was extracted with dichloromethane for three times. The organic phase was washed with brine, dried over anhydrous $Na_2SO_4$. The solvent was removed by using rotary evaporation. The residue was purified by using column chromatography with DCM:MeOH (v/v)=50:1 to 20:1, to afford 320 mg of compound B6, yield 87%. $^1$H NMR (300 MHz, $CDCl_3$) δ3.56-3.58 (m, 1H), 2.10-2.15 (m, 4H), 1.62-1.68 (m, 16H), 1.45-1.52 (m, 8H), 1.17-1.23 ppm (m, 8H).

(5) 1-(5-(6-oxo-7-heterospiro[4.8]tridecane-8-yl)pentyl)cyclopentanecarboxylic acid (Compound 5)

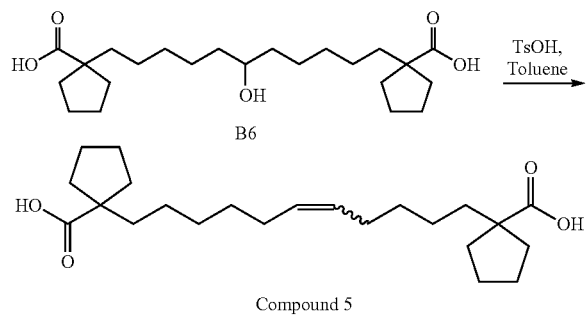

A solution of compound B6 (40 mg, 0.22 mmol) in 80 mL of toluene was added 30 mg of p-toluenesulfonic acid. The reaction mixture was refluxed for 2 days, monitored by TLC. After the reaction was completed, the solvent was removed by using rotary evaporation. The residue was purified by using column chromatography with DCM:MeOH (v/v)= 100:1 to give compound B7, 30 mg, yield 85%. $^1$H NMR (300 MHz, $CDCl_3$) δ5.33-5.34 (m, 1H), 2.15-2.17 (m, 4H), 1.97-2.09 (m, 4H), 1.62-1.64 (m, 12H), 1.40-1.49 (m, 6H), 1.26-1.29 ppm (m, 10H).

In the same way, the following compounds were obtained:

Compound 1 was prepared by replacing reagent B1 with ethyl isobutyrate:
$^1$H NMR (300 MHz, $CDCl_3$) δ5.34-5.36 (m, 2H), 1.95-1.98 (m, 4H), 1.50-1.55 (m, 4H), 1.21-1.42 (m, 10H), 1.18 ppm (s, 12H).

Compound 2 was prepared by replacing reactant B1 with ethyl isobutyrate, and replacing reactant B2 with 1,6-dibromohexane: $^1$H NMR (300 MHz, $CDCl_3$) δ5.34-5.35 (m, 2H), 1.96-1.98 (m, 4H), 1.50-1.52 (m, 4H), 1.21-1.42 (m, 14H), 1.17 ppm (s, 12H).

Compound 3 was prepared by replacing the reactant B1 with ethyl isobutyrate, and replacing the reactant B2 with 1,4-dibromobutane: $^1$H NMR (300 MHz, $CDCl_3$) δ5.29-5.38 (m, 2H), 1.92-1.95 (m, 4H), 1.43-1.52 (m, 4H), 1.21-1.42 (m, 6H), 1.13 ppm (s, 12H).

Compound 4 was prepared by replacing the reactant B1 with ethyl isobutyrate, and replacing the reactant B2 with 1,7-dibromoheptane: $^1$H NMR (300 MHz, $CDCl_3$) δ5.34-5.35 (m, 2H), 1.94-1.95 (m, 4H), 1.48-1.52 (m, 6H), 1.21-1.42 (m, 16H), 1.17 ppm (s, 12H).

Compound 6 was prepared by replacing the reactant B2 with 1,6-dibromohexane: $^1$H NMR (300 MHz, $CDCl_3$) δ5.33-5.34 (m, 2H), 2.12-2.16 (m, 4H), 1.94-2.02 (m, 4H), 1.62-1.64 (m, 12H), 1.40-1.49 (m, 6H), 1.26-1.29 ppm (m, 12H).

Compound 7 was prepared by replacing the reactant B2 with 1,4-dibromobutane: $^1$H NMR (300 MHz, $CDCl_3$) δ5.33-5.42 (m, 2H), 2.14-2.18 (m, 4H), 1.96-1.99 (m, 4H), 1.62-1.64 (m, 10H), 1.40-1.49 (m, 6H), 1.26-1.29 ppm (m, 6H).

Compound 8 was prepared by replacing the reactant B2 with 1,7-dibromoheptane: $^1$H NMR (300 MHz, $CDCl_3$) δ5.33-5.36 (m, 2H), 2.12-2.16 (m, 4H), 1.96-1.99 (m, 4H), 1.62-1.64 (m, 12H), 1.40-1.49 (m, 6H), 1.26-1.29 ppm (m, 16H).

Compound 9 was prepared by replacing the reactant B1 with ethyl 2-phenylpropionate: $^1$H NMR (300 MHz, $CDCl_3$) δ7.26-7.36 (m, 10H), 5.34-5.36 (m, 2H), 2.02-2.22 (m, 4H), 1.86-2.03 (m, 4H), 1.54 (s, 6H), 1.22-1.42 (m, 10H).

Compound 10 was prepared by replacing the reactant B1 with ethyl cyclohexylcarboxylate: $^1$H NMR (300 MHz, $CDCl_3$) δ5.32-5.34 (m, 2H), 2.06-2.09 (m, 4H), 1.94-1.98 (m, 4H), 1.45-1.65 (m, 10H), 1.15-1.45 (m, 18H), 0.88-0.96 ppm (m, 2H).

Compound 11 was prepared by replacing the reactant B1 with ethyl cyclobutanecarboxylate: $^1$H NMR (300 MHz, $CDCl_3$) δ5.32-5.34 (m, 2H), 2.43-2.45 (m, 4H), 1.96-1.99 (m, 4H), 1.81-1.92 (m, 10H), 1.76-1.1.82 (m, 4H), 1.25-1.36 ppm (m, 8H).

Compound 12
$^1$H NMR (300 MHz, $CDCl_3$) δ5.34-5.36 (m, 2H), 2.36-2.43 (t, 4H), 1.96-2.05 (m, 4H), 1.53-1.65 (m, 4H), 1.22-1.40 (m, 10H).

Compound 13 was prepared by replacing the reactant B1 with ethyl cyclobutylate, and replacing reactant B2 with 1,6-dibromohexane: $^1$H NMR (300 MHz, $CDCl_3$) δ5.33-

5.35 (m, 2H), 2.43-2.45 (m, 4H), 1.96-1.99 (m, 4H), 1.81-1.92 (m, 10H), 1.75-1.1.82 (m, 4H), 1.11-1.28 ppm (m, 12H).

Compound 14 was prepared by replacing the reactant B1 with ethyl 2-methylbutyrate: ¹H NMR (300 MHz, CDCl₃) δ5.33-5.35 (m, 2H), 1.96-2.02 (m, 4H), 1.60-1.78 (m, 4H), 1.38-1.58 (m, 4H), 1.22-1.40 (m, 8H), 1.11 (s, 6H), 0.85 ppm (t, 6H).

Compound 15 was prepared by replacing the reactant B1 with cyclopentene-1-carboxylic acid ethyl ester, replacing the reactant B2 with 1,6-dibromohexane: ¹H NMR (300 MHz, CDCl₃) δ5.60 (S, 4H), 5.32-5.34 (m, 2H), 2.88-2.94 (d, J=16 Hz, 4H), 2.27-2.32 (d, J=16 Hz, 4H), 1.94-1.96 (m, 4H), 1.67-1.72 (m, 4H), 1.19-1.38 ppm (m, 18H).

Compound 16 was prepared by replacing the reactant B1 with cyclopentene-1-carboxylic acid ethyl ester: ¹H NMR (300 MHz, CDCl₃) δ5.60 (S, 4H), 5.32-5.34 (m, 2H), 2.88-2.93 (d, J=16 Hz, 4H), 2.27-2.32 (d, J=16 Hz, 4H), 1.96-1.99 (m, 4H), 1.67-1.73 (m, 4H), 1.25-1.38 ppm (m, 14H).

Compound 17 was prepared by replacing the reactant B1 with ethyl 2-phenyl-propionate, and replacing the reactant B2 with 1,6-dibromohexane: ¹H NMR (300 MHz, CDCl₃) δ7.26-7.40 (m, 10H), 5.34-5.36 (m, 2H), 2.02-2.22 (m, 4H), 1.86-2.03 (m, 4H), 1.55 (s, 6H), 1.18-1.42 (m, 14H).

Compound 18 was prepared by replacing the reactant B1 with ethyl 2-phenyl-propionate, and replacing the reactant B2 with 1,7-dibromoheptane: ¹H NMR (300 MHz, CDCl₃) δ7.23-7.38 (m, 10H), 5.34-5.36 (m, 2H), 2.02-2.22 (m, 4H), 1.86-2.03 (m, 4H), 1.55 (s, 6H), 1.18-1.42 (m, 18H).

Compound 19 was prepared by replacing the reactant B1 with ethyl 2-methylbutyrate, and replacing the reactant B2 with 1,6-dibromohexane: ¹H NMR (300 MHz, CDCl₃) δ5.33-5.35 (m, 2H), 1.96-2.02 (m, 4H), 1.58-1.78 (m, 4H), 1.38-1.58 (m, 4H), 1.22-1.40 (m, 14H), 1.11 (s, 6H), 0.86 ppm (t, 6H).

Compound 20 was prepared by replacing the reactant B1 with ethyl 2-methylbutyrate, and replacing the reactant B2 with 1,7-dibromoheptane: ¹H NMR (300 MHz, CDCl₃) δ5.33-5.35 (m, 2H), 1.96-2.02 (m, 4H), 1.58-1.70 (m, 4H), 1.38-1.50 (m, 4H), 1.22-1.40 (m, 18H), 1.11 (s, 6H), 0.86 ppm (t, 6H).

Compound 21 was prepared by replacing the reactant B1 with ethyl cyclohexylcarboxylate, and replacing the reactant B2 with 1,6-dibromohexane: ¹H NMR (300 MHz, CDCl₃) δ5.32-5.34 (m, 2H), 2.04-2.05 (m, 4H), 1.94-1.98 (m, 4H), 1.45-1.65 (m, 12H), 1.15-1.45 (m, 22H).

Compound 22 was prepared by replacing the reactant B1 with ethyl cyclohexylcarboxylate, and replacing the reactant B2 with 1,7-dibromoheptane: ¹H NMR (300 MHz, CDCl₃) δ5.32-5.34 (m, 2H), 2.04-2.08 (m, 4H), 1.96-2.01 (m, 4H), 1.45-1.65 (m, 12H), 1.23-1.45 (m, 26H).

Preparation Example 2 Preparation of (Z)-2,2,14,14-tetramethyl-7-yne-pentadecanedioic acid (Compound 24)

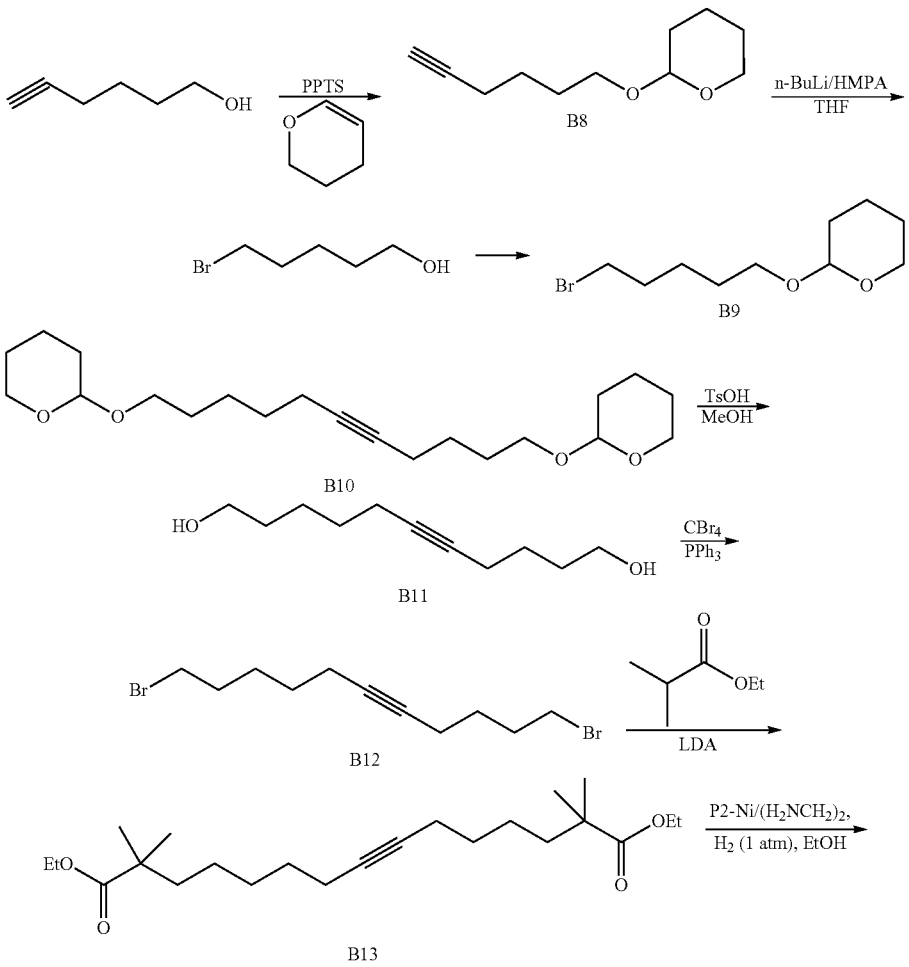

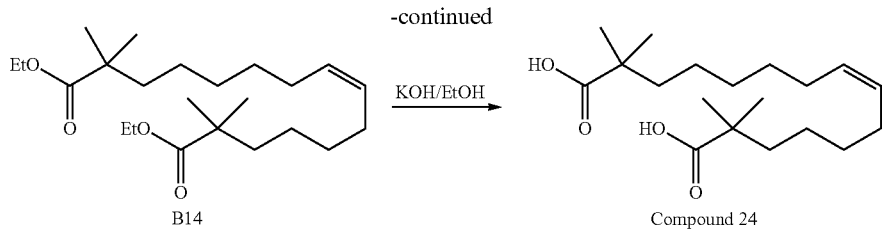

B14 → Compound 24 (KOH/EtOH)

(1) Preparation of 2-(hex-5-ynyloxy)tetrahydro-2H-pyran (B8)

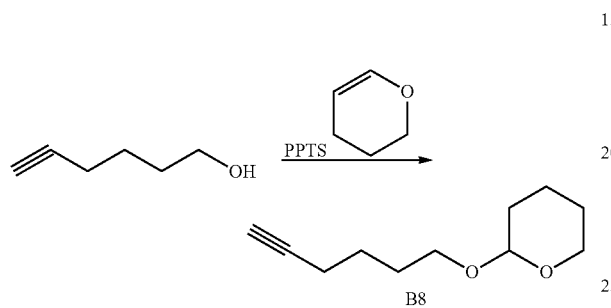

The compound 5-hexyn-1-ol (9 g, 91 mmol) and pyridinium p-toluenesulfonate (25.1 g, 100 mmol) were dissolved in 100 mL of DCM, and added THF (12.5 mL, 126 mmol). The reaction mixture was stirred at room temperature for overnight. Progress of reaction was monitored by TLC. Upon completion, most of the DCM was removed until about 30 mL left. Then, the residue was added 100 mL of ethyl ether and stirred for 0.5 h. The solid was filtered off, and washed with ethyl ether. The filtrate was concentrated, and then, purified using column chromatography with PE:EA (v/v)=50/1 to give the compound B8 as an oil, 18 g, yield >100%.

(2) Preparation of 2-(5-bromopentyl)tetrahydro-2H-pyran (B9)

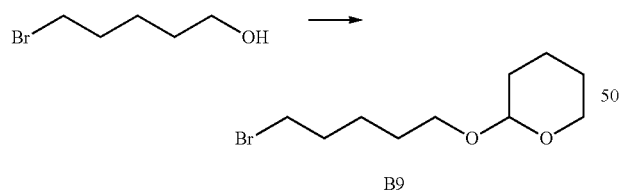

The compound 5-bromo-1-pentanol (15.1 g, 91 mmol) and pyridinium p-toluenesulfonate (25.1 g, 100 mmol) were dissolved in 100 mL of DCM, added THF (12.5 mL, 126 mmol). The reaction mixture was stirred at room temperature for overnight. Progress of reaction was monitored by TLC. Upon completion, most of the DCM was removed until about 30 mL left. Then, the residue was added 100 mL of ethyl ether and stirred for 0.5 h. The solid was filtered off, and washed with ethyl ether. The filtrate was concentrated, and then, purified using column chromatography with PE:EA (v/v)=50/1 to give the compound B9, 18 g, yield 79%.

(3) Preparation of 2,2'-(undec-5-yne-1,11-diylbis(oxy))bis(tetrahydro-2H-pyran) (B10)

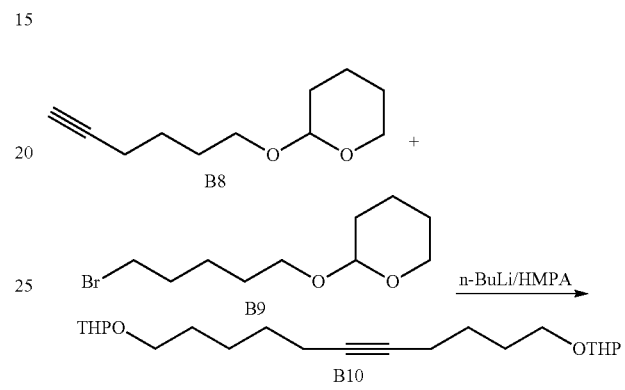

Compound B8 (5.4 g, 30 mmol) was dissolved in 40 mL of anhydrous THF, cooled to −40° C. n-butyl lithium (19 mL, 30.4 mmol) was added dropwise (in about 0.5 h) to the solution, then 10 mL of HMPA was added. The reaction was stirred at −40° C. for 1 hour, then, a solution of compound B9 (7.78 g, 31 mmol) in 10 mL THF was added and stirred for 1 hour. The reaction was slowly warmed to room temperature and stirred overnight. The reaction was quenched by the addition of a saturated aqueous solution of ammonium chloride. After the addition, the two phase were separated, and the separated aqueous phase was extracted one time with EtOAc. The combined organic layers were washed with brine, dried, concentrated, and then, purified using column chromatography with PE:EA (v/v)=20/1→10/1→5/1 to give the compound B10, 8.5 g, yield 80%.

(4) Preparation of undeca-5-yne-1,11-diol (B11)

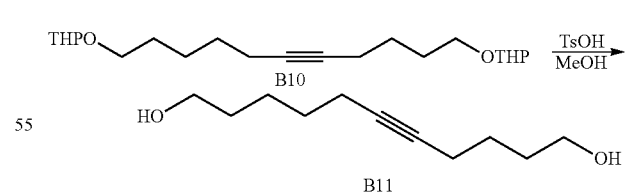

Compound B10 (3 g, 8.5 mmol) was dissolved in 100 mL of methanol and 10 mL of water, and added p-toluenesulfonic acid (300 mg). The reaction mixture was stirred at room temperature for overnight. Progress of reaction was monitored by TLC. Upon completion, most of the methanol was removed. Then, the residue was diluted with water and extracted twice with ethyl ether. The combined organic layers were washed with water and brine, dried, concentrated, and then, purified by column chromatography with PE:EA (v/v)=2/1→1/1→1/2 to give the compound B11, 1.1 g, yield 70%.

(5) Preparation of 1,11-dibromo-undec-5-yne (B12)

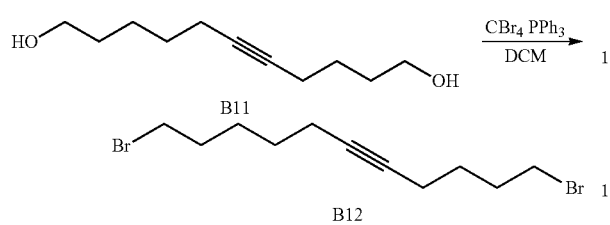

Compound B11 (1.1 g, 5.9 mmol) and carbon tetrabromide (5.95 g, 17.9 mmol) were dissolved in 30 mL of anhydrous DCM, cooled to 0° C., then, added a solution of triphenylphosphine (4.7 g, 17.9 mmol) in 10 mL of DCM dropwise. After stirred at room temperature for 1 h, the reaction was completed. The reaction mixture was condensed into about 15 mL, added 50 mL of ethyl ether and stirred for 0.5 h. The solid was filtered off. The filtrate is concentrated, and purified using column chromatography with PE:EA=30/1 to give the bromo compound B12, 1.84 g, yield 100%.

(6) Preparation of diethyl 2,2,14,14-tetramethylpentadec-7-ynedioate (B13)

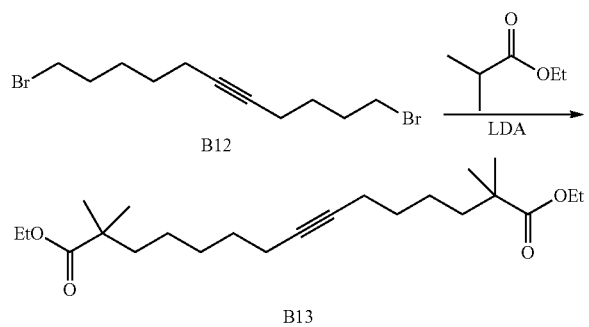

Compound B12 (1.84 g, 5.9 mmol) and ethyl isobutyrate (2.73 g, 23.6 mmol) were dissolved in 50 mL of anhydrous THF, cooled to 0° C., then, added LDA (15.7 mL, 23.6 mmol) dropwise (in about 0.5 h). The reaction was stirred at 0° C. for 1 hour, then, slowly warmed to room temperature and stirred overnight. Progress of reaction was monitored by TLC. Upon completion, the reaction was quenched by the addition of a saturated aqueous solution of ammonium chloride. After the addition, the two phase were separated, and the separated aqueous phase was extracted two times with EtOAc. The combined organic layers were washed with water and brine, dried, concentrated, and then, purified using column chromatography with PE:EA (v/v)=50/1→20/1 to give the compound B13, 1.8 g, yield 80%.

(7) Preparation of diethyl-(Z)-2,2,14,14-tetramethyl-7-ynyl-pentadecanedate (B14)

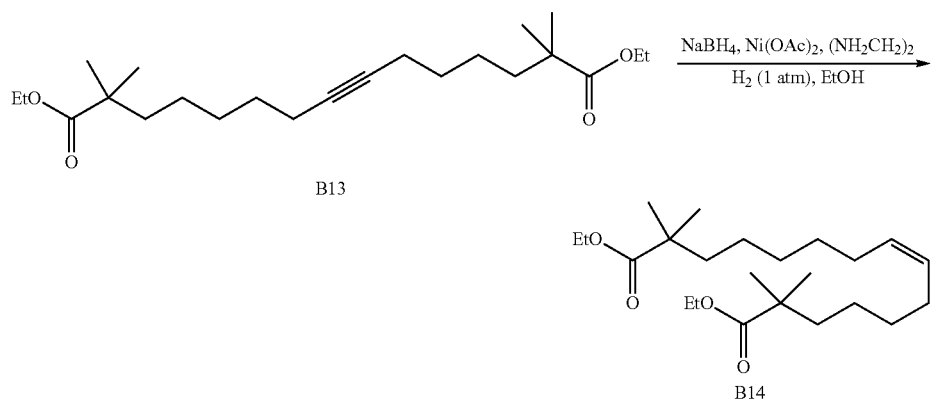

Under one atm. of $H_2$, nickel acetate (749 mg, 3 mmol) was suspended in 20 mL of absolute ethanol, sodium borohydride (114 mg, 3 mmol) was quickly added. The flask was evacuated and flushed with hydrogen twice and the solution turned black. After stirred at room temperature for 15 minutes, the mixture was added ethylenediamine (0.45 mL, 6 mmol) and a solution of compound B13 (1.8 g, 4.7 mmol) in 10 mL of absolute ethanol. The reaction was stirred at room temperature for 2 h, monitored by TLC. Upon completion, the reaction was diluted with 50 mL of ethyl ether, filtered through Celite. The filtrate was concentrated and purified by using column chromatography with PE/EA (v/v) =50/1 to obtain product B14, 1.7 g, yield 95%.

(8) Preparation of (Z)-2,2,14,14-tetramethyl-7-ene-pentadecanedioic acid (Compound 24)

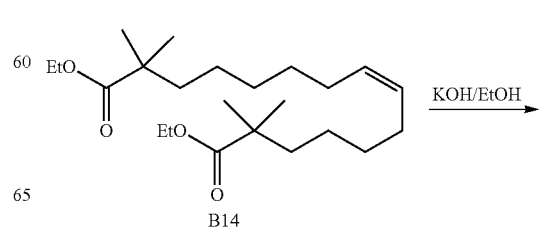

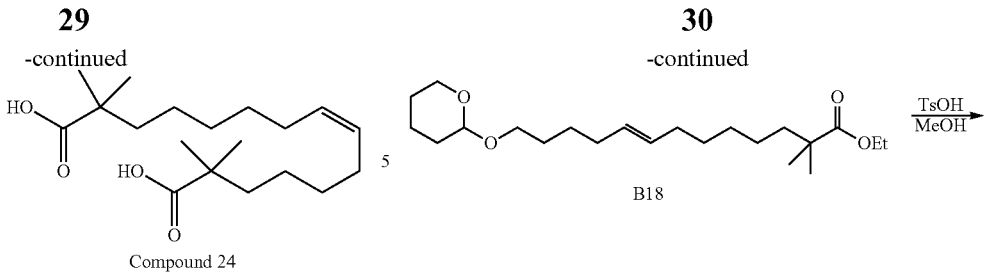

Compound 24

Compound B14 (1.7 g, 4.45 mmol) was dissolved in 50 mL of ethanol and added 10 mL of an aqueous solution of KOH (2 g, 35 mmol). The reaction mixture was refluxed for 6 hours, and monitored by TLC. After the reaction was completed, the mixture was cooled to room temperature, and most of the ethanol was removed by rotary evaporation. The residue was diluted with water (40 mL) and extracted with ethyl ether twice to remove impurities. The mixture was adjusted to acidity by adding 2N HCl, and extracted with DCM for four times. The combined organic phase was washed with water and brine, dried, concentrated and purified using column chromatography with DCM/MeOH (v/v)=100/1 to give compound 24, 1.1 g.

Compound 24

$^1$H NMR (600 MHz, DMSO) δ5.31-5.32 (m, 2H), 1.96-1.98 (m, 4H), 1.40-1.44 (m, 4H), 1.22-1.30 (m, 4H), 1.18-1.22 (m, 6H), 1.06 ppm (s, 12H).

Compound 23

$^1$H NMR (300 MHz, CD$_3$Cl) δ5.31-5.32 (m, 2H), 1.96-1.98 (m, 4H), 1.40-1.44 (m, 4H), 1.18-1.22 (m, 8H), 1.06 ppm (s, 12H).

Compound 25

$^1$H NMR (300 MHz, CD$_3$Cl) δ5.30-5.32 (m, 2H), 1.96-1.98 (m, 4H), 1.40-1.45 (m, 4H), 1.18-1.22 (m, 12H), 1.06 ppm (s, 12H).

Preparation Example 3: Preparation of (E)-2,2,14,14-tetramethyl-7-ene-pentadecanedioic acid (Compound 30)

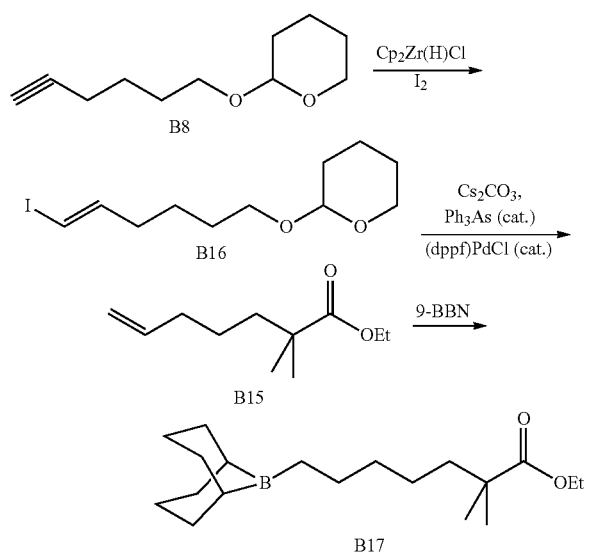

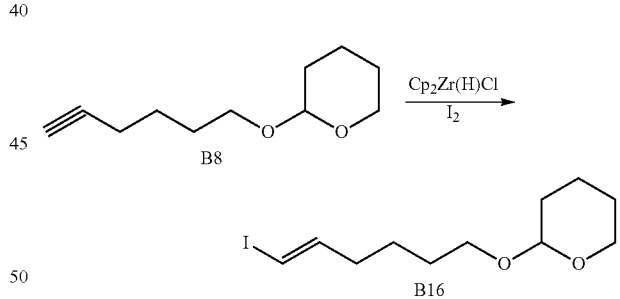

Compound 30

(1) Preparation of (E)-2-(6-iodohexene-5-enyloxy) tetrahydro-2H-pyran (B16)

Compound B8 (460 mg, 2.5 mmol) was dissolved in 20 mL of dry THF and Schwartz's reagent (chloridobis(η5-cyclopentadienyl)hydridozirconium) (1.63 g, 6.3 mmol) was added. The reaction was stirred at room temperature for 2 h, then, cooled to 0° C., and adding a saturated solution of I$_2$ in DCM (30 mL). After stirred at 0° C. for 10 min, the reaction was quenched with 20 mL of saturated Na$_2$S$_2$O$_3$ solution. The mixture was extracted two times with DCM. The combined organic layers were washed with water and brine, dried, concentrated, and then, purified by using column chromatography with PE/EA (v/v)=50/1→20/1 to obtain the product B16, 450 mg, yield 58%.

(2) Preparation of (E)-ethyl-2,2-dimethyl-13-(tetrahydro-2H-pyran-2-oxo)tridec-8-enoate (B18)

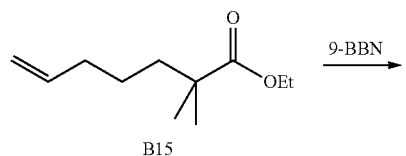

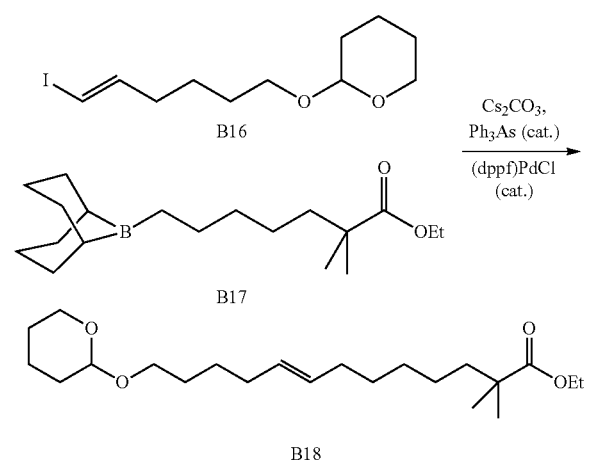

Under the protection of argon gas, 2 mL of 9-BBN solution 0.5M in THF was added to compound B15 (60 mg, 0.35 mmol). After stirred at room temperature for 2 hours, the reaction mixture was added 2 mL of solution of compound B16 in DMF, and then added Cs$_2$CO$_3$ (156 mg), AsPh$_3$ (24 mg) and 1 mL of water in order. After evacuated and flushed with argon gas for 5 min, Pd(dppf)Cl$_2$ (20 mg) was added. The reaction was stirred at room temperature overnight. The reaction was diluted with 30 mL of ethyl ether, washed with water and brine, dried, concentrated. The residue was purified by using column chromatography with PE/EA (v/v)=50/1→20/1 to give the product B18, 54 mg, yield 90%.

(3) Preparation of (E)-Ethyl-13-hydroxy-2,2-dimethyltridec-8-enoate (B19)

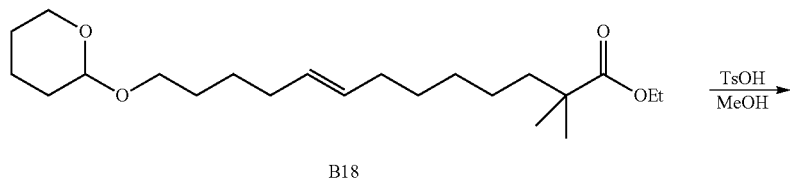

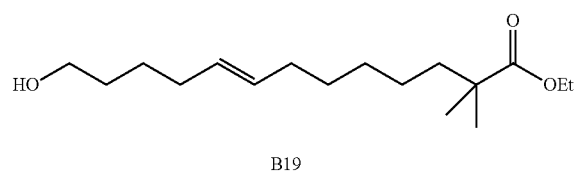

Compound B19 (350 mg, 0.95 mmol) was dissolved in 10 mL of methanol and 1 mL of water, and added p-toluenesulfonic acid (25 mg). The reaction was stirred at room temperature overnight, monitored by TLC. Upon completion, most of the methanol was removed. The residue was diluted with water, and extracted twice with ethyl ether. The combined organic phase was washed with water and brine, dried, concentrated and purified using column chromatography with PE:EA (v/v)=4/1 to give a product B19, 200 mg, yield 78%

(4) Preparation of (E)-ethyl-13-bromo-2,2-dimethyltridec-8-enoate (B20)

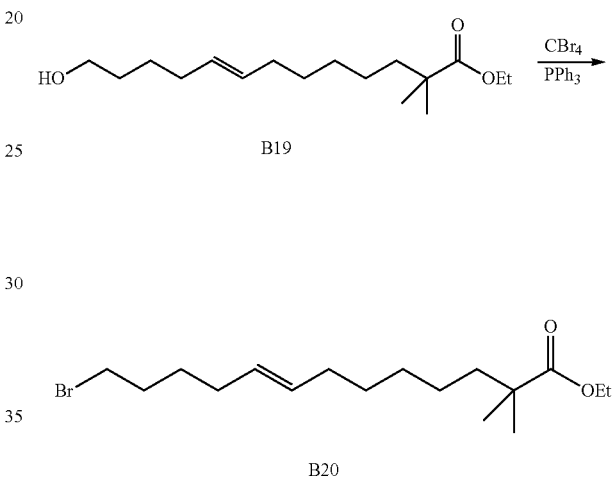

Compound B19 (200 mg, 0.7 mmol) and carbon tetrabromide (302 mg, 0.91 mmol) were dissolved in 10 mL of anhydrous DCM. Cooled to 0° C., the reaction was added 2 mL of triphenylphosphine (256 g, 0.98 mmol) in DCM, and stirred for 1 h. After the reaction was complete, the reaction mixture was concentrated and purified using column chromatography with PE:EA (v/v)=20/1 to give a bromo compound B20, 206 mg, yield 87%.

(5) Preparation of diethyl-(E)-2,2,14,14-tetramethyl-7-ene-pentadecanedate (B21)

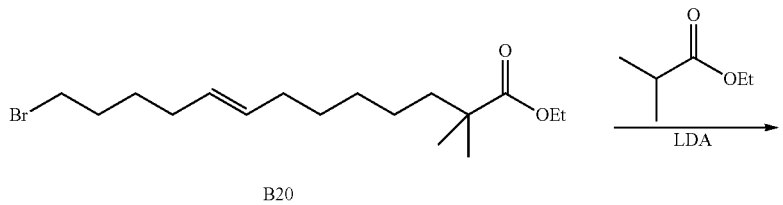

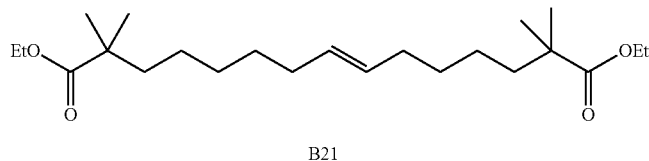

Compound B20 (200 mg, 0.57 mmol) and ethyl isobutyrate (100 mg, 0.86 mmol) were dissolved in 10 mL of anhydrous THF. Cooled to 0° C., the reaction was added LDA (0.6 mL, 0.9 mmol) dropwise (in about 0.5 h). After stirred at 0° C. for 1 h, the reaction was warmed to room temperature and stirred overnight. Progress of reaction was monitored by TLC. Upon completion, the reaction was quenched by the addition of a saturated aqueous solution of ammonium chloride. After the addition, the two phase were separated, and the separated aqueous phase was extracted two times with EtOAc. The combined organic layers were washed with water and brine, dried, concentrated, and then, purified using column chromatography with PE:EA (v/v)=50/1, the product B21, 177 mg, yield 80%.

(6) Preparation of (E)-2,2,14,14-tetramethyl-7-alkenyl-pentadecanedioic acid (Compound 30)

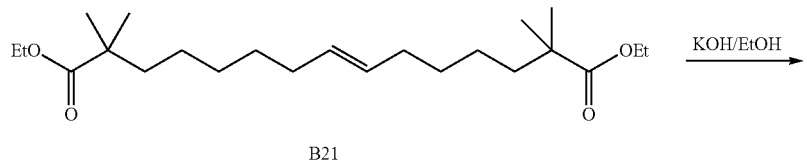

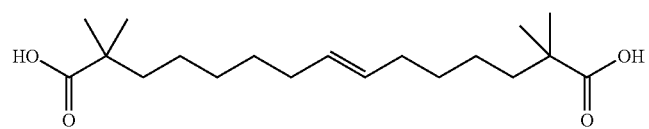

Compound 30

Compound B21 (107 mg, 0.28 mmol) was dissolved in 10 mL of EtOAc, added 2 mL of an aqueous solution of KOH (200 mg, 3.5 mmol). The reaction mixture was refluxed for 6 hours, and monitored by TLC. After the reaction was completed, the mixture was cooled to room temperature, and most of the ethanol was removed by rotary evaporation. The residue was diluted with water (10 mL) and extracted two times with ethyl ether to remove impurities. The aqueous phase was adjusted to acidity by adding 2N HCl, and extracted with DCM for four times. The combined organic phase was washed with water and brine, dried, concentrated and purified using column chromatography with DCM/MeOH (v/v)=100/1 to obtain the compound, 70 mg.

Compound 30

$^1$H NMR (600 MHz, DMSO) δ5.35-5.36 (m, 2H), 1.92-1.94 (m, 4H), 1.40-1.43 (m, 4H), 1.27-1.29 (m, 4H), 1.17-1.19 (m, 6H), 1.18 ppm (s, 12H).

Preparation Example 4 Preparation of (Z)-2,2,7,8,14,14-hexamethylpentadecene-7-butenedioic acid (Compound 28)

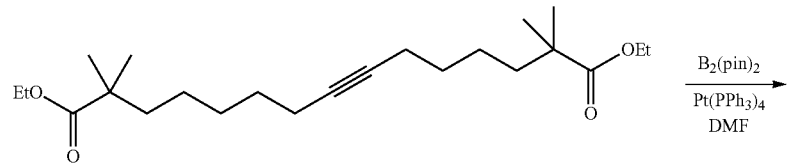

B13

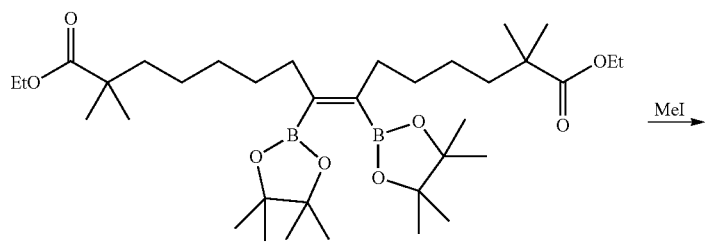

B22

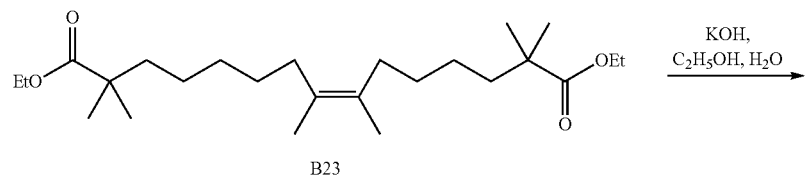

B23

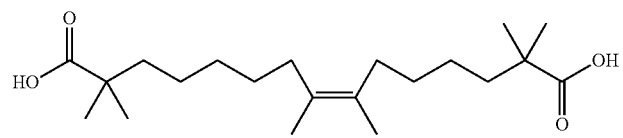

Compound 28

(1) Preparation of (Z)-Diethyl-2,2,14,14-tetramethyl-7,8-bis(4,4,5,5-tetramethyl-1,3,2-dioxaboron heterocyclic pentan-2-yl)pentadecene-7-enedioate (B22)

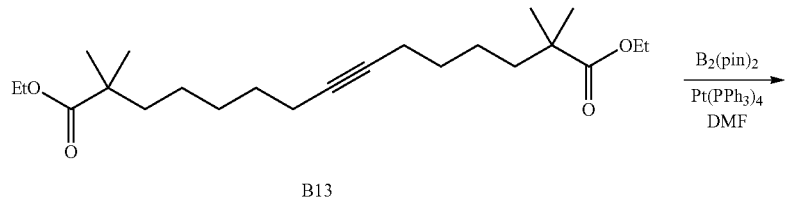

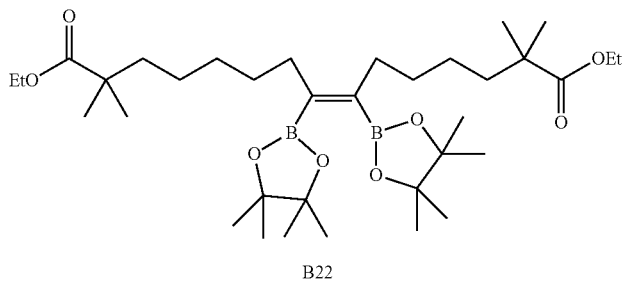

Bis(pinacolato)diboron (483 mg, 1.9 mmol) and tetrakis(phenylphosphine) platinum (70 mg) were placed in a 25 mL round bottom flask. After evacuated and flushed with argon gas three times, B13 (660 mg, 1.74 mmol) of 10 mL DMF was added dropwise. The reaction was heated at 80° C. overnight. The mixture was diluted with water, and extracted with ethyl ether. The combined organic phase was washed with water and brine, dried. The solvent was removed using rotary evaporation. The residue was purified using column chromatography with PE/EA (v/v)=10/1 to give the product B22, 1 g, yield 90%.

$^1$H NMR (300 MHz, CDCl$_3$) δ4.08-4.11 (m, 4H), 2.13-2.16 (m, 4H), 1.40-1.43 (m, 4H), 1.25-1.33 (m, 10H), 1.27 (m, 24H), 1.17-1.19 (t, 6H), 1.13 ppm (s, 12H)

(2) Preparation of (Z)-diethyl-2,2,7,8,14,14-hexamethylpentadecene-7-butenedioate (B23)

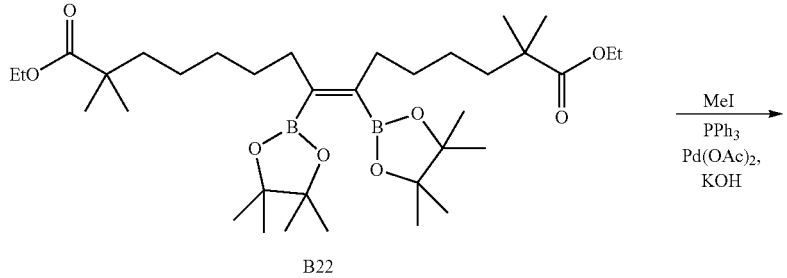

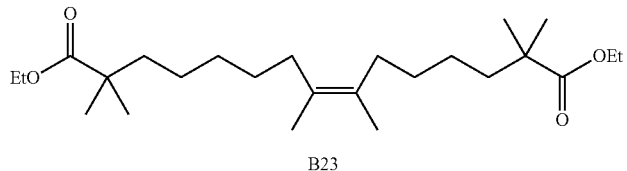

Compound B22 (150 mg, 0.23 mmol), iodomethane (0.1 mL) and triphenylphosphine (10 mg) were dissolved in 1 mL of dioxane. After evacuated and flushed with argon gas three times, the mixture was added palladium acetate (20 mg), 0.2 mL of an aqueous solution of KOH (40 mg). The reaction mixture was heated at 90° C. for 12 h, diluted with water and ethyl acetate, and extracted three times with ethyl acetate. The combined organic phase was washed with water and brine, dried, and concentrated. The residue was purified using column chromatography with PE/EA (v/v)=50/1 to give the product B23, 30 mg, yield 31%.

(3) Preparation of (Z)-2,2,7,8,14,14-hexamethylpentadecene-7-butenedioic acid (Compound 28)

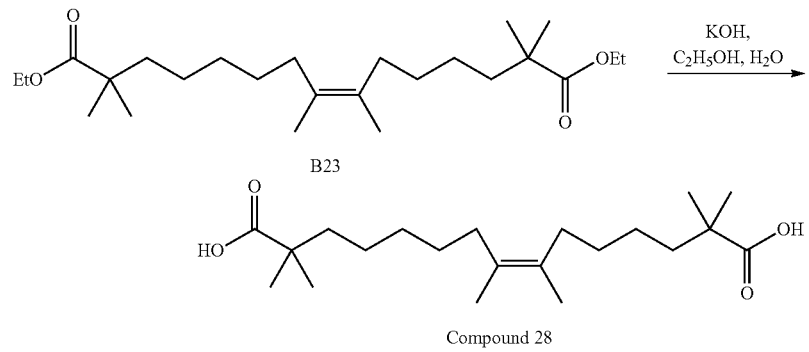

Compound B23 (30 mg, 0.07 mmol) was dissolved in 5 mL of ethanol and added 1 mL of an aqueous solution of KOH (50 mg, 0.89 mmol). The reaction mixture was refluxed for 6 hours, and monitored by TLC. After the reaction was completed, the mixture was cooled to room temperature, and most of the ethanol was removed by rotary evaporation. The residue was diluted with water (4 mL) and extracted with ethyl ether twice to remove impurities. The aqueous phase was adjusted to acidity by adding 2N HCl, and extracted with DCM for four times. The combined organic phase was washed with water and brine, dried, concentrated and purified using column chromatography with DCM/MeOH (v/v)=100/1 to get 15 mg compound 28.

Compound 28

$^1$H NMR (300 MHz, CDCl$_3$) δ 1.94-1.96 (m, 4H), 1.58 (s, 6H), 1.48-1.50 (m, 4H), 1.25-1.33 (m, 12H), 1.13 ppm (s, 12H).

Preparation Example 5 Preparation of 7-(2-(5-carboxy-5-methylhexyl)cyclopropyl)-2,2-dimethylheptanoic acid (Compound 29)

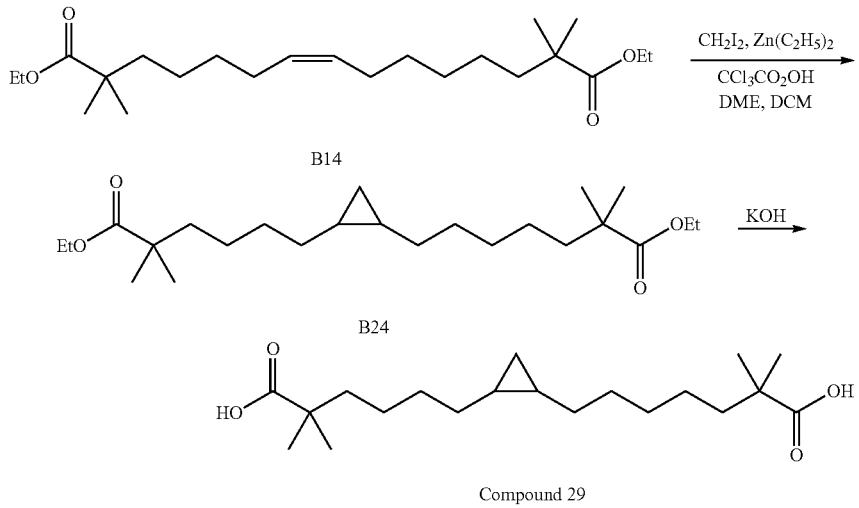

(1) Preparation of Ethyl-7-(2-(6-ethoxy-5,5-dimethyl-6-oxohexyl) cyclopropyl)-2,2-dimethylheptanoate (B24)

Under a nitrogen atmosphere, 1 mL of dry DCM was added to a 20 mL reaction flask, then added diethylzinc (1 mL, 1 mmol), and cooled to −40° C. After 5 min, 0.5 mL of diiodomethane (0.54 g, 2 mmol) solution in DCM was added dropwise. After reacted at −40° C. for 1 h, the reaction was added trichloroacetic acid (16 mg, 0.1 mmol) and DME (45 mg, 0.5 mmol), then, warmed to −15° C. and stirred for 1 h. 0.5 mL of B14 solution (193 mg, 0.5 mmol) in DCM was added. After the addition, the reaction mixture was stirred at room temperature overnight. The reaction was quenched by the addition of a saturated aqueous solution of ammonium chloride and extracted three times with ethyl acetate. The combined organic layers were washed with brine, dried, concentrated, and then, purified using column chromatography with PE:EA (v/v)=50/1 to give the product B24, 120 mg, yield 60%.

(2) Preparation of 7-(2-(5-carboxy-5-methylhexyl) cyclopropyl)-2,2-dimethylheptanoic acid (Compound 29)

Compound B24 (100 mg, 0.25 mmol) was dissolved in 5 mL of ethanol and added 1 mL of an aqueous solution of KOH (10 mg, 0.18 mmol). The reaction mixture was refluxed for 6 hours, and monitored by TLC. After the reaction was completed, the mixture was cooled to room temperature, and most of the ethanol was removed by rotary evaporation. The residue was diluted with water (4 mL) and extracted with ethyl ether twice to remove impurities. The aqueous phase was adjusted to acidity by adding 2N HCl, and extracted with DCM for four times. The combined organic phase was washed with water and brine, dried, concentrated and purified by using column chromatography with DCM/MeOH (v/v)=100/1 to give compound 29, 65 mg.

Compound 29
$^1$H NMR (300 MHz, CDCl$_3$) δ 1.1.45-1.52 (m, 4H), 1.21-1.43 (m, 16H), 1.18 (s, 12H), 0.65-0.70 ppm (m, 2H)

Preparation Example 6
(Z)-2,2,17,17-tetramethyl-octadecyl-9-enedioic acid (Compound 26)

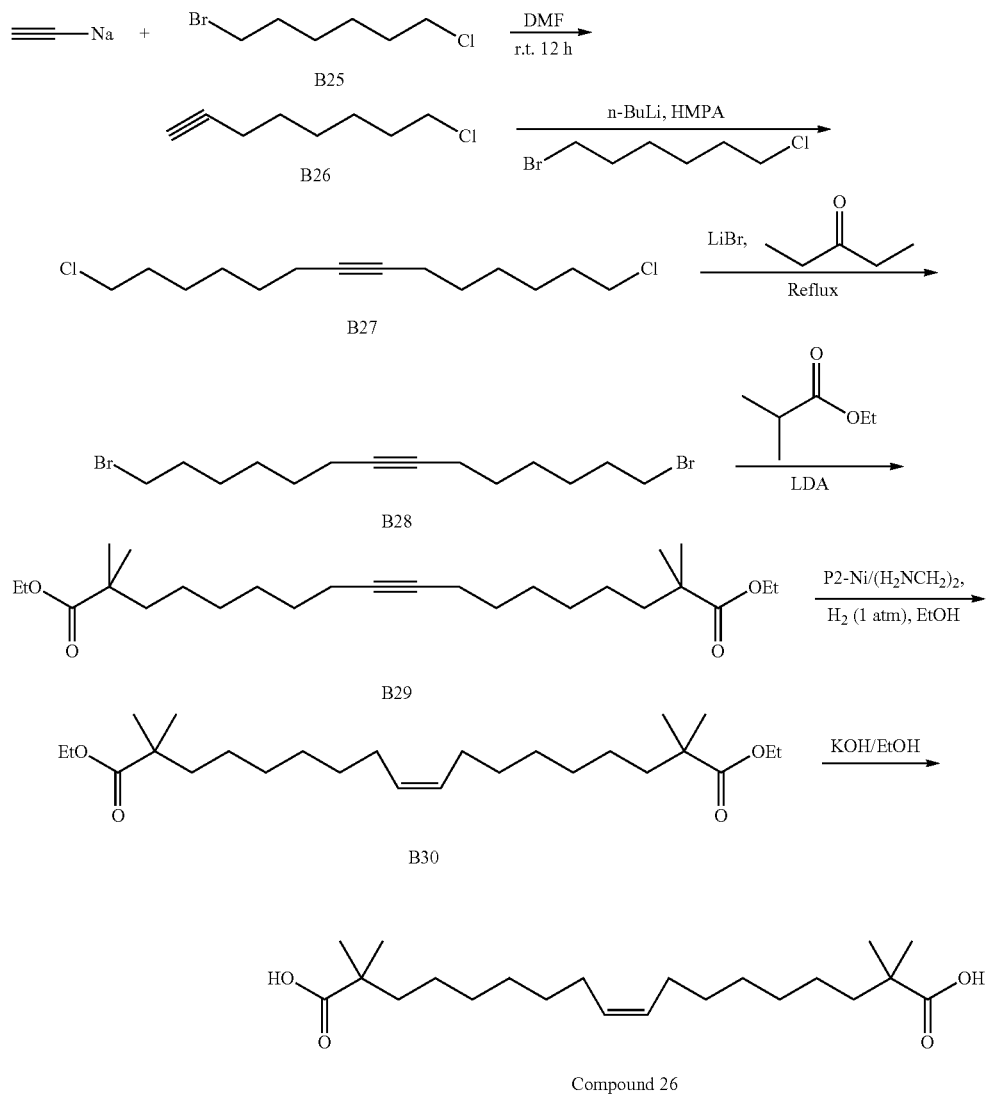

Compound 26

(1) Preparation of 8-chloro-oct-1-yne (B26)

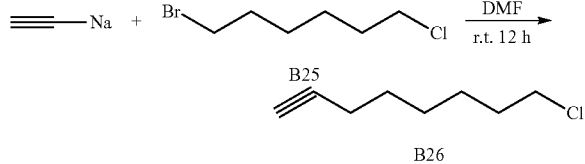

Compound B25 (1.6 g, 8 mmol) was dissolved in 8 mL of DMF. After cooled to 0° C., the reaction mixture was added a solution of sodium acetylide in xylene (18%, 12 mmol). After the addition, the reaction mixture was stirred at room temperature overnight. The reaction was added water and ethyl ether, and separated. The organic layers were washed with water and brine, dried, concentrated, and then, distilled under reduced pressure to obtain 1.2 g of B26.

(2) Preparation of 1,14-dichloro-tetradec-7-yne (B27)

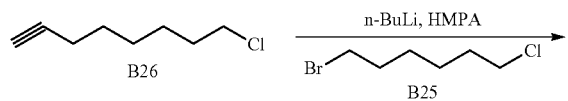

Compound B26 (1.2 g, 8 mmol) was dissolved in 15 mL of anhydrous THF, cooled to −40° C., n-butyllithium (5.2 mL, 1.6 M, 8.3 mmol) was added dropwise. After the addition, HMPA (4 mL) was added and stirred for 1 h. After that, the reaction mixture was added a solution of B25 (1.6 g, 8.2 mmol) in 5 mL THF, and stirred at room temperature overnight. The reaction was quenched by the addition of a saturated aqueous solution of ammonium chloride. After the addition, the two phase were separated, and the separated aqueous phase was extracted with EtOAc. The combined organic layers were washed with brine, dried, concentrated, and then, purified using column chromatography with PE:EA (v/v)=100/1 to give the product B27, 1.6 g, yield 80%.

(3) Preparation of 1,14-dibromo-tetradec-7-yne (B28)

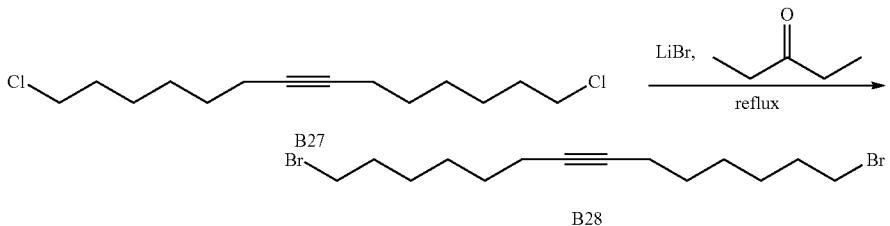

Compound B27 (100 mg, 0.4 mmol) and lithium bromide (688 mg, 8 mmol) were dissolved in 3-pentanone (7 mL). The reaction mixture was heated with an oil bath at 120° C. for 6 h. Then, 3-pentanone was removed by rotary evaporation and added water and EtOAc. The two phase were separated, and the organic phase was washed with brine, dried, concentrated to get a 120 mg of crude product which was held for use in the next step without purification.

(4) Preparation of diethyl-2,2,17,17-tetramethyl-7-ene-octadecyl-dicarboxylate (B29)

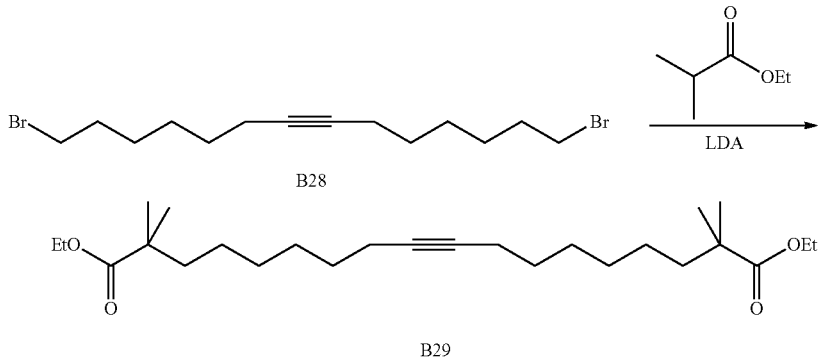

Compound B28 (120 mg, 0.34 mmol) and ethyl isobutyrate (238 g, 2 mmol) were dissolved in 5 mL anhydrous THF, cooled to 0° C., and then added LDA (1.3 mL, 2 mmol) dropwise (in about 0.5 h). After stirred at 0° C. for 1 h, the reaction was warmed to room temperature and stirred overnight. Progress of reaction was monitored by TLC. Upon completion, the reaction was quenched by the addition of a saturated aqueous solution of ammonium chloride. After the addition, the two phase were separated, and the separated aqueous phase was extracted two times with EtOAc. The combined organic layers were washed with water and brine, dried, concentrated, and then, purified using column chromatography with PE:EA (v/v)=50/1 to give the product B29, 80 g, yield 56%.

(5) Preparation of (Z)-diethyl-2,2,17,17-tetramethyl-7-ene-octadecyl-dicarboxylate (B30)

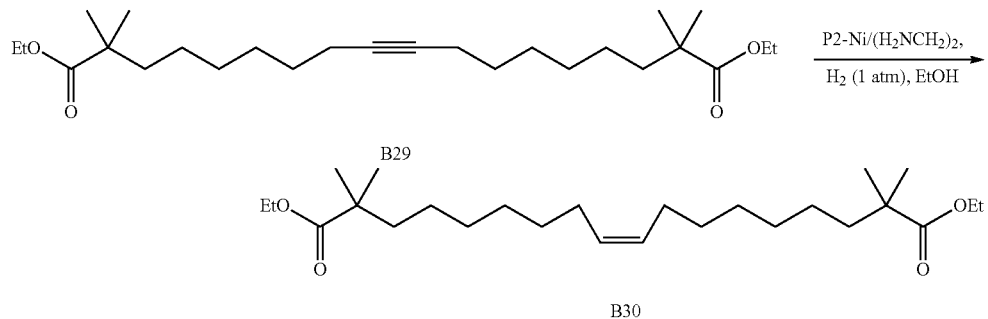

Under one atm. of $H_2$, nickel acetate (25 mg, 0.1 mmol) was suspended in 1 mL of absolute ethanol, sodium borohydride (7 mg, 0.18 mmol) was quickly added. The flask was evacuated and flushed with hydrogen twice and the solution became black. After stirred at room temperature for 15 minutes, the mixture was added ethylenediamine (15 μL), and a solution of compound B29 (75 mg, 0.17 mmol) in 1 mL absolute ethanol. The reaction was stirred at room temperature for 2 h, monitored by TLC. Upon completion, the reaction was diluted with 10 mL of ethyl ether, filtered through Celite. The filtrate was concentrated and purified using column chromatography with PE/EA (v/v)=50/1 to obtain product B30, 45 mg, yield 60%.

(6) Preparation of (Z)-2,2,17,17-tetramethyl-7-ene-octadecyl-diacid (Compound 26)

The compound B30 (40 mg, 0.01 mmol) was dissolved in 5 mL of ethanol, added 1 mL of an aqueous solution of KOH (100 mg, 1.7 mmol). The reaction mixture was refluxed for 6 hours, and monitored by TLC. After the reaction was completed, the mixture was cooled to room temperature, and most of the ethanol was removed by rotary evaporation. The residue was diluted with water (4 mL) and extracted with ethyl ether twice to remove impurities. The aqueous phase was adjusted to acidity by adding 2N HCl, and extracted with DCM for four times. The combined organic phase was washed with water and brine, dried, concentrated and purified using column chromatography with DCM/MeOH (v/v)= 100/1 to give 20 mg of compound 26.

Compound 26

$^1$H NMR (300 MHz, $CD_3Cl$) δ5.30-5.32 (m, 2H), 1.98-2.02 (m, 4H), 1.48-1.53 (m, 4H), 1.18-1.22 (m, 16H), 1.06 ppm (s, 12H)

Preparation Example 7 6,6'-(cyclohexene-1,2-diyl) bis(2,2-dimethylhexanoic acid) (Compound 27)

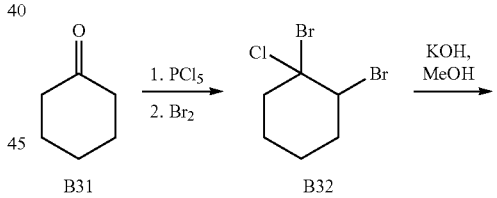

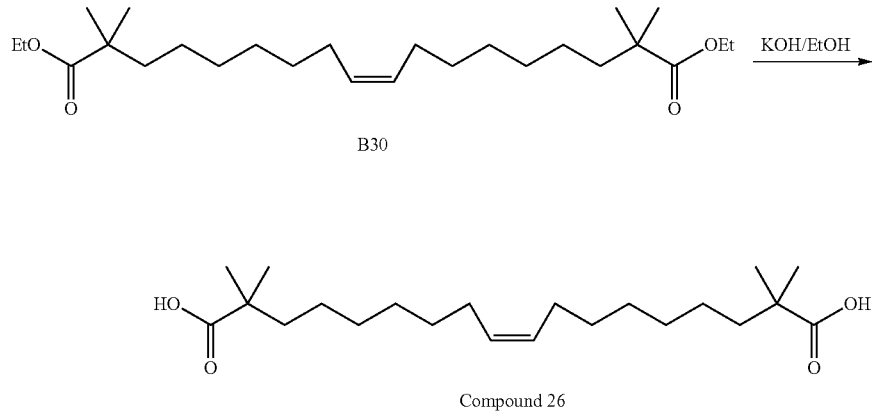

Compound 26

(2) 1,2-dibromocyclohex-1-ene

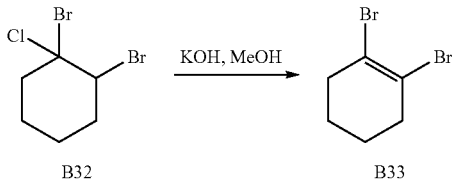

A solution of compound B32 (2.2 g) in MeOH (8 mL) was added to a solution of KOH (1 g, 18 mmol) in MeOH (8 mL) under refluxing. The reaction mixture was refluxed for 3 hours, and cooled to room temperature. The mixture was adjusted to acidity by adding 6N HCl, added water and extracted with DCM for two times. The combined organic phase was washed with water and brine, dried, concentrated and purified using column chromatography with petroleum ether to give compound B33, 1.1 g, two steps yield 23%.

(3) 1,2-diiodocyclohex-1-ene

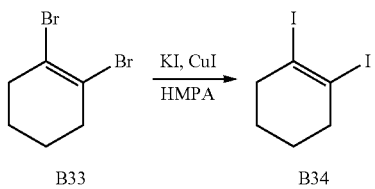

Compound B33 (700 mg, 2.9 mmol), potassium iodide (4.9 g, 30 mmol) and cuprous iodide (2.85 g, 15 mmol) were placed in 8 mL of HMPA. The reaction was heated with an oil bath at 120° C. for 15 h. Cooled to room temperature, the mixture was added 20 mL of 2N HCl and 20 mL of benzene. The two phase were separated, and the aqueous phase was extracted with benzene. The combined organic phase was added sodium thiosulfate 10% solution, washed with brine, dried and concentrated. The residue was purified using column chromatography with petroleum ether to give 828 mg of compound B34, yield 85%.

(4) diethyl 6,6'-(cyclohex-1-ene-1,2-diyl)bis(2,2-dimethylhexanoate)

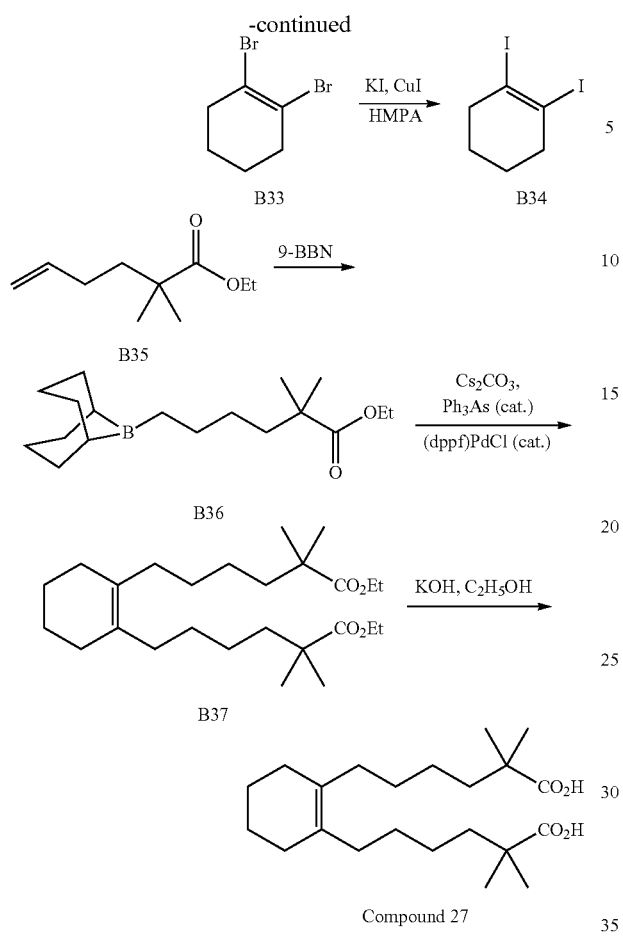

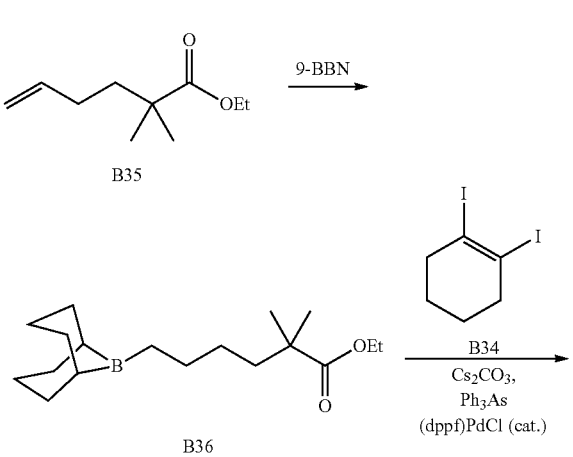

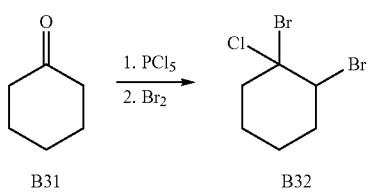

Compound 27

(1) 1,2-dibromo-1-chlorocyclohexane

Phosphorus pentachloride (4.37 g, 21 mmol) was suspended in 10 mL of chloroform, cooled to 0° C., and added to a solution of compound B31 (1.96 g, 20 mmol) in 10 mL of chloroform. After the addition, the mixture was stirred at room temperature for 2 h, then refluxed for 2 h. After then, the reaction mixture was poured on 50 g of ice, added NaHCO$_3$. The organic phase was separated, and the aqueous phase was extracted with DCM. The combined organic phase was washed with saturated sodium bicarbonate solution and brine. The mixture was dried over anhydrous Na$_2$SO$_4$, concentrated, then added 5 mL of DCM. After cooled to −5° C., the mixture was slowly added bromine (2.08 g, 13 mmol) in a dropwise manner. After stirred at −5° C. for 10 min, the mixture was added sodium thiosulfate 10% solution and washed with brine, dried and concentrated, and purified using column chromatography with petroleum ether to give Compound B32, 2.2 g.

-continued

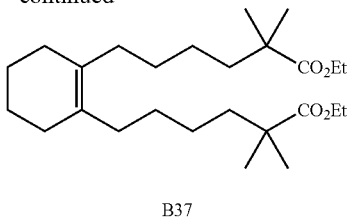

B37

Under the protection of argon gas, 3.5 mL of 9-BBN solution 0.5M in THF was added to compound B35 (100 mg, 0.58 mmol). After stirred at room temperature for 2 hours, the reaction mixture was added 2 mL of solution of compound B34 (50 mg, 0.15 mmol) in DMF, and then added $Cs_2CO_3$ (156 mg), $AsPh_3$ (24 mg) and 1 mL of water in order. After evacuated and flushed with and argon gas for 5 min, $Pd(dppf)Cl_2$ (30 mg) was added. The reaction was stirred at room temperature overnight. The reaction was diluted with 30 mL of ethyl ether, washed with water and brine, dried, concentrated. The residue was purified using column chromatography with PE/EA (v/v)=50/1 to give the product B37, 70 mg, yield 70%.

(5) Preparation of 6,6'-(cyclohexene-1,2-diyl)bis(2, 2-dimethylhexanoic acid (Compound 27)

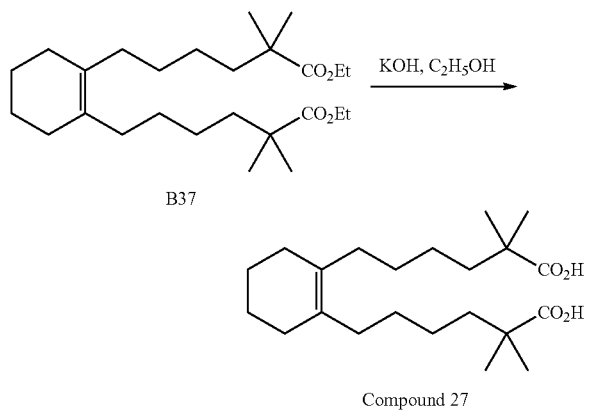

The compound B37 (40 mg, 0.01 mmol) was dissolved in 5 mL of ethanol, added 1 mL of an aqueous solution of KOH (100 mg, 1.7 mmol). The reaction mixture was refluxed for 6 hours, and monitored by TLC. After the reaction was completed, the mixture was cooled to room temperature, and most of the ethanol was removed by rotary evaporation. The residue was diluted with water (4 mL) and extracted with ethyl ether twice to remove impurities. The aqueous phase was adjusted to acidity by adding 2N HCl, and extracted with DCM for four times. The combined organic phase was washed with water and brine, dried, concentrated and purified by using column chromatography with DCM/MeOH (v/v)=100/1 to give 20 mg of compound 27.

Compound 27
$^1H$ NMR (300 MHz, $CD_3Cl$) δ1.89-1.91 (m, 8H), 1.52-1.54 (m, 8H), 1.19-1.22 (m, 8H), 1.06 ppm (s, 12H).

Experimental Example

1. Evaluation of the effects of compounds on AMPK signaling pathway in human HepG2 hepatoma cells (1) Detection purpose: To detect whether the fatty acid compound is a small molecule compound that can promote phosphorylation of α subunit T172 site of AMPK and phosphorylation of classical site ACC1 S79 of AMPK in human hepatoma cell HepG2.

(2) Experimental principle: In the cell, small molecule compounds activate AMPK, which promotes phosphorylation of the α-subunit T172 site and the downstream substrate acetyl CoA carboxylase (ACC) Ser-79site.

(3) Detection reagents: Total AMPK, phospho-AMPKα (T172), phospho-ACC (S79), and Total ACC antibody were purchased from Cell Signaling Technology.

(4) Experimental method:

1) Human hepatoma cells HepG2 cells were inoculated into a 24-well plate at a density of 300,000 per mL. After grew adhering to the wall 12 hours, they were replaced on serumfree highsugar medium for 12 hours. Compounds 1 to 30 prepared by the present invention (in 1‰ DMSO, 50 μM) were separately added to treat for 6 hours (1‰ DMSO as a negative control). The cells to be harvested were washed with pre-cooled PBS. 1×SDS gel loading buffer (50 mM Tris-HCl (pH 6.8), 100 mM DTT, 2% SDS, 10% glycerol, 0.1% bromophenol blue) was added. Lyse cells on ice for 10 minutes (24 well plates, 100 μL per well).

2) The sample was taken in a 1.5 mL EP tube, heated at 100 C for 10 minutes, and then centrifuged at 12000 g for 10 minutes. The supernatant was subjected to SDS-PAGE electrophoresis under the following conditions, concentrated gel: 80 volts, separation gel: 120 volts.

3) After the electrophoresis, the protein was transferred to a nitrocellulose membrane (constant pressure 100 V, 100 min) using Biorad wet electrical transduction system. After the desired band was cut, the strip was blocked in a blocking solution (TBST, containing 5% BSA) for 1 hour at room temperature. The strips were placed in a solution of primary antibody and incubated overnight at 4° C.

4) On next day, the target strip was placed in TBST and washed at room temperature for 10 minutes (3 times). The strips were then incubated in a solution of secondary antibody (goat anti-rabbit and goat anti-mouse 1:5000 in TBST) for 1 hour at room temperature. Then, membrane was washed with TBST for 10 minutes (3 times) and exposed with ECL reagent.

Figure 2:
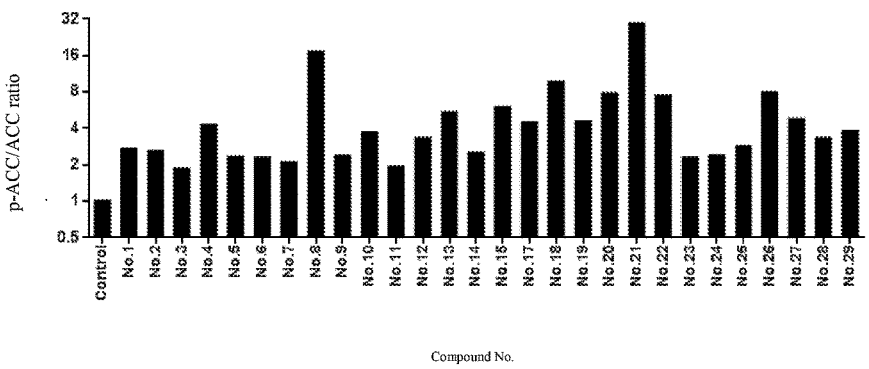
FIG. 2 is a bar graph of the compound promoting phosphorylation of ACC in human HepG2 liver cancer cells.

(5) Experimental Results:

As shown in FIGS. 1 and 2, among the fatty acid compounds obtained, most of the compounds (50 μM) significantly promoted phosphorylation of AMPK and ACC. The effects of promotion AMPK phosphorylation of compounds, such as 4, 5, 8, 18, 19, 20, were over 4 times comparing with the negative control. The effects of promotion ACC phosphorylation of compounds like 4, 8, 18, 20, 21, 22 was over 4 times compare with the negative control.

2. To Investigate the Effect of Compounds on Glucose Output in Primary Hepatocytes of C57bl/6j Mice.

(1) Test purpose: To test whether the fatty acid compounds can inhibit hepatocyte glucose output on primary hepatocytes of C57bl/6j mice.

(2) Experimental principle: Small molecule compounds act on mouse primary hepatocytes, inhibit gluconeogenesis, and then affect the glucose output of cells into the medium. The effect of compounds on gluconeogenesis is evaluated by detecting the glucose concentration in the medium after the treatment of different compounds.

(3) Detection reagent: The glucose detection kit was purchased from Shanghai Mind Bioengineering Co., Ltd.

(4) Experimental method:

1) the primary hepatocytes of C57bl/6j mice were isolated and inoculated into a 24-well plate at a density of 300,000 per mL. After grew adhering to the wall for 6 hours, they were replaced on serumfree highsugar medium for 12 hours. Compounds 1 to 30 prepared by the present invention (in 1‰ DMSO, 50 μM) were separately added to treat for 6 hours (1‰ DMSO as a negative control). The medium was gently mixed, 50 μL of supernatant was taken from every well, and glucose concentration was measured by a glucose oxidase assay kit.

2) The medium was discarded. The cells was washed with PBS, spin dried, added 200 μL of 250 mM sodium hydroxide solution. Lyse the cells for 30 minutes, then take the lysate. The protein concentration was determined using coomassie blue staining.

3) The amount of glucose output in the cells is corrected by the protein concentration, and the effect of the compound on the glucose output of the hepatocytes is compared.

Figure 3:
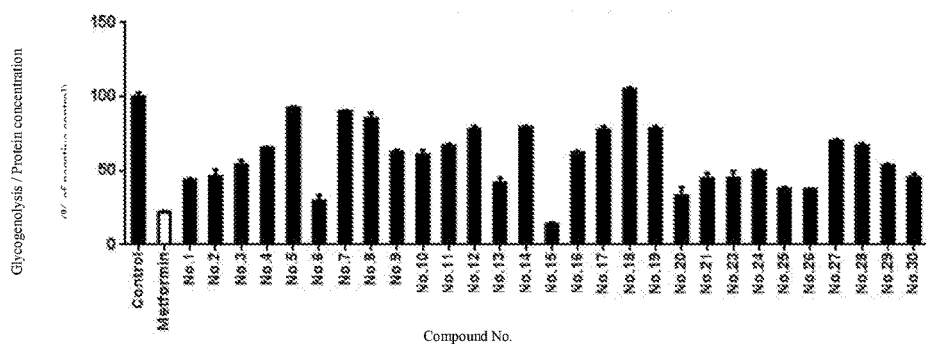
FIG. 3 is a bar graph of the compound inhibiting sugar output of mouse primary hepatocytes.

(5) Experimental Results:

After treating the primary hepatocytes with the compounds obtained, no obvious abnormalities in the morphology of the hepatocytes and a decrease in the protein concentration were observed. It is indicated that the compounds had no significant toxic effects at the sub-dose and treatment time. As shown in FIG. 3, most of these fatty acid compounds have a significant inhibitory effect on glucose output. The effects of gluconeogenesis inhibition of compounds, including 1, 2, 6, 13, 15, 20, more than 50% of the negative control (FIG. 3).

The invention claimed is:

1. A fatty acid compound of formula II, or a pharmaceutically acceptable salt thereof:

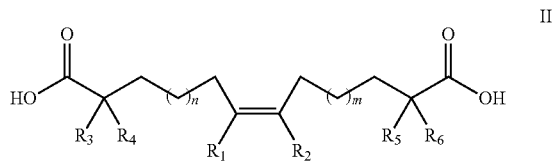

wherein $R_1$ and $R_2$ are each independently H, C1~C4 alkyl or phenyl;

$R_3$, $R_4$, $R_5$, and $R_6$ are each independently C1~C4 alkyl or phenyl;

alternatively, $R_5$ and $R_6$ together with their adjacent carbon atoms form a C3~C7 cycloalkyl group, or together with their adjacent carbon atom form a C3~C7 cycloalkenyl group, alternatively, $R_3$ and $R_4$ together with their adjacent carbon atoms form a C3~C7 cycloalkyl group, or together with their adjacent carbon atoms form a C3~C7 cycloalkenyl group;

m, n are each independently 1, 2, 3, 4, 5 or 6, the double bond is either cis or trans.

2. The fatty acid compound of formula II according to claim 1, or a pharmaceutically acceptable salt thereof, wherein the said fatty acid compound is selected from:

Compound 1

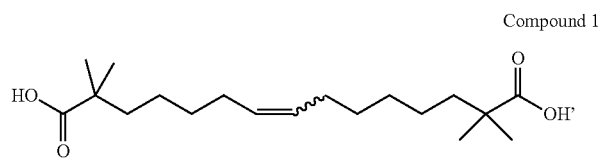

Compound 2

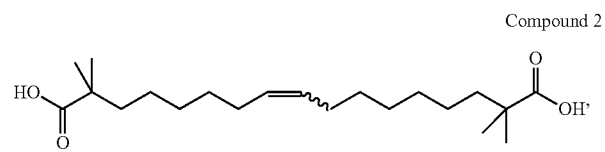

Compound 3

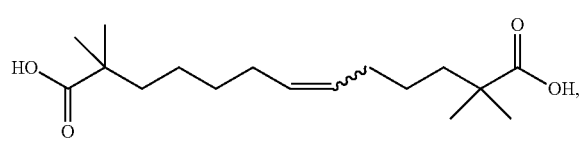

Compound 4

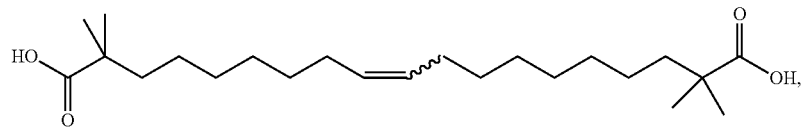

Compound 5

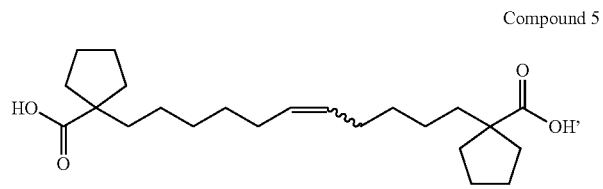

Compound 6

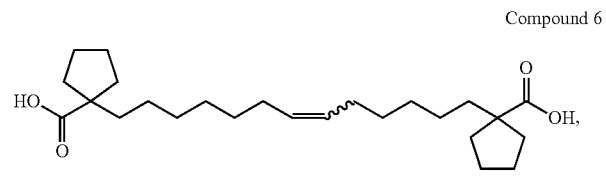

Compound 7

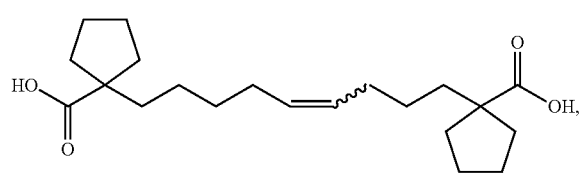

-continued
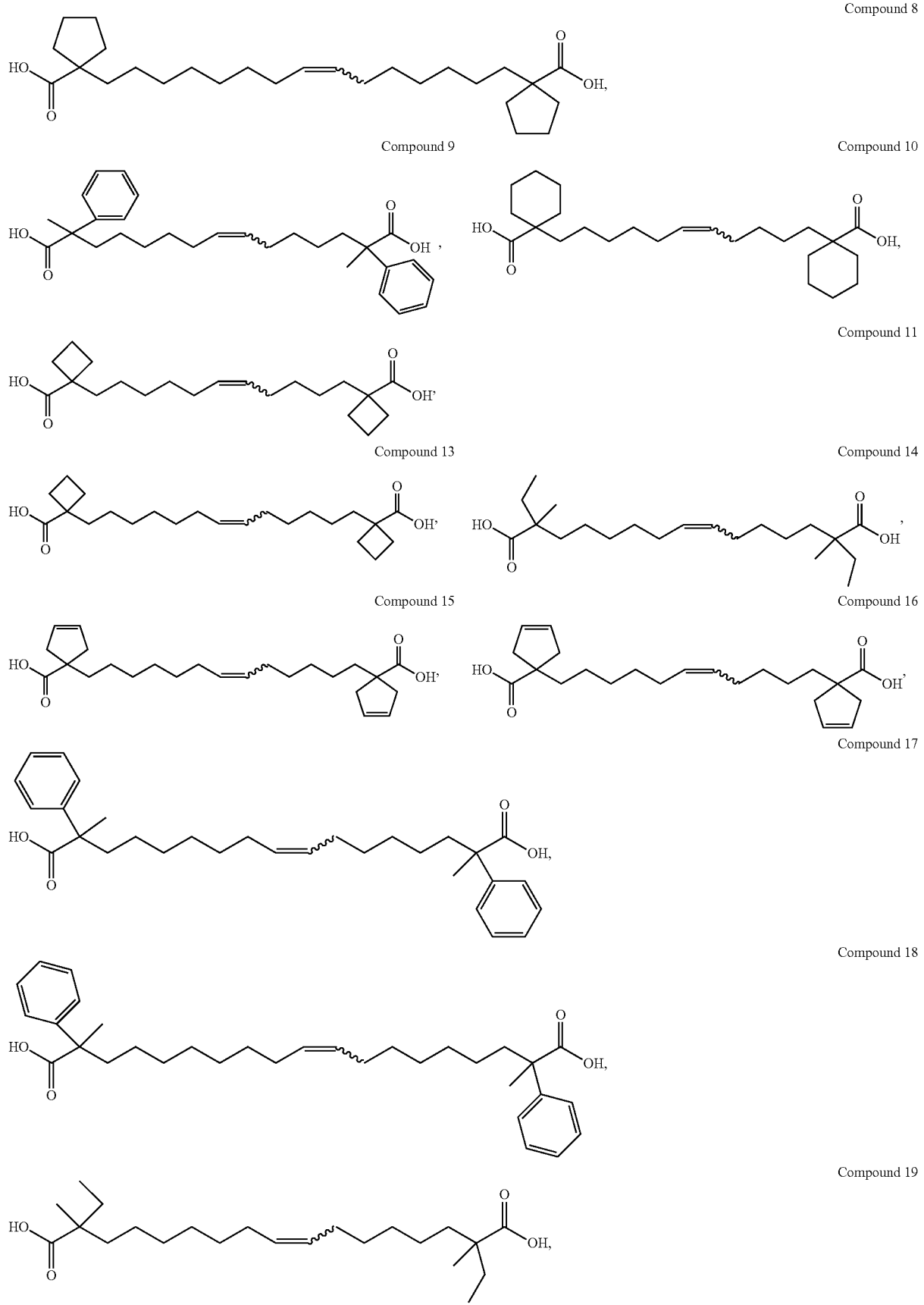

-continued
Compound 20
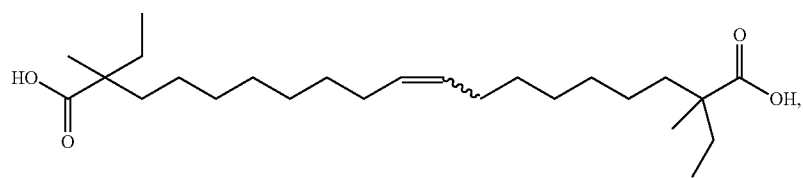
Compound 21
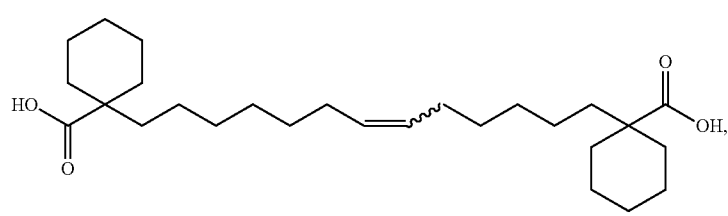
Compound 22
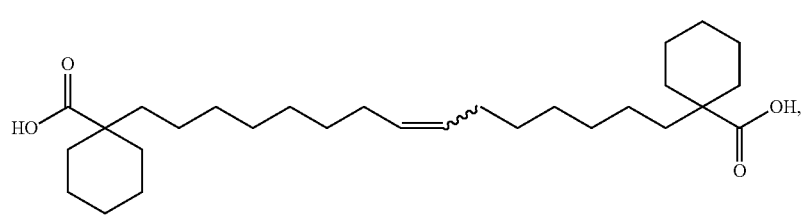
| Compound 23 | Compound 24 |
|---|---|
| 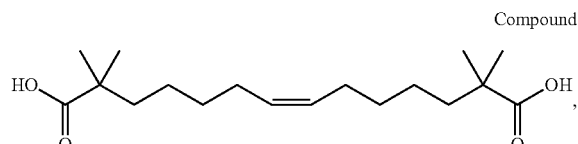 | 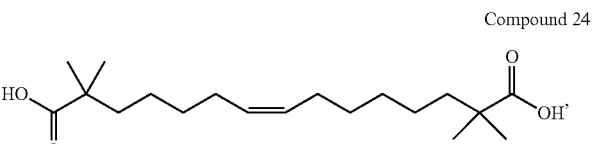 |
| Compound 25 | Compound 26 |
| 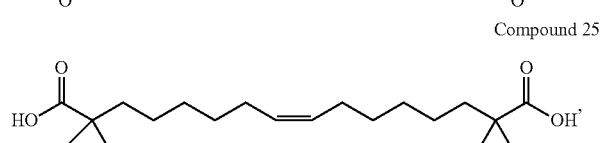 | 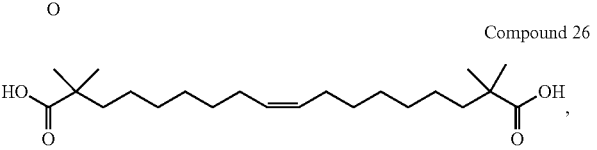 |
| Compound 28 | Compound 30 |
| 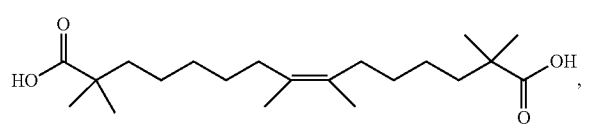 | |
3. A method for preparing the fatty acid compound of formula II according to claim 1, wherein the method comprises the following steps:
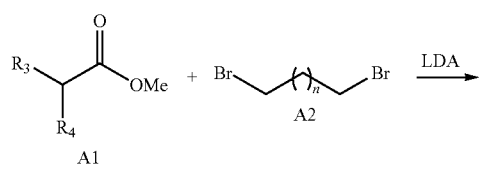
-continued
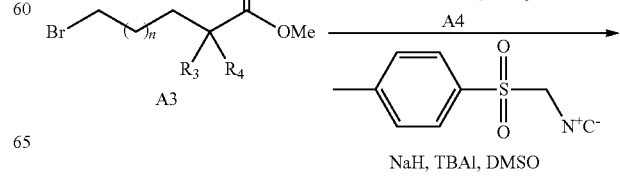

-continued

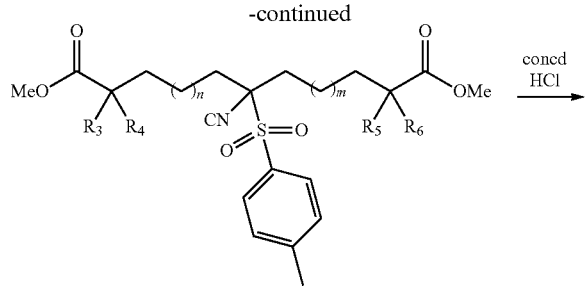

A5

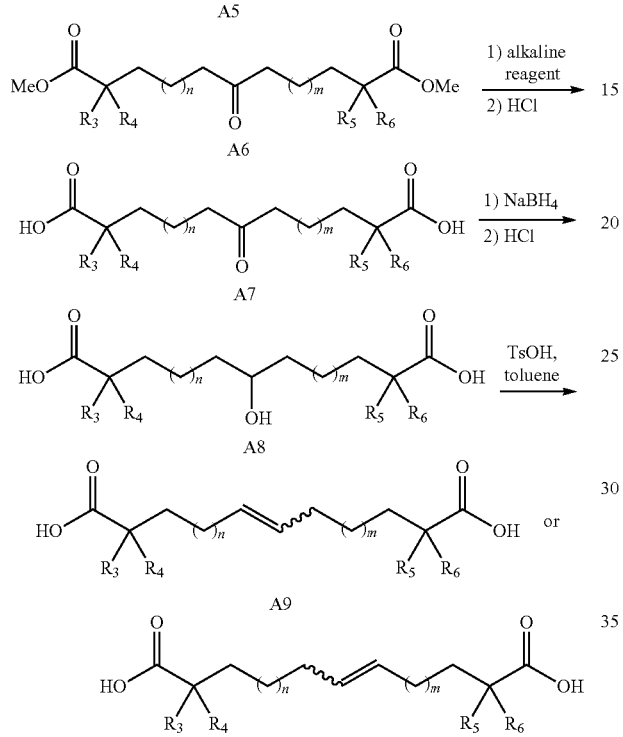

(1) reacting substituted ethyl acetate A1 with dibromoalkane A2 in the presence of lithium diisopropylamide and an organic solvent to obtain intermediate A3; under the same conditions, replacing A1 with

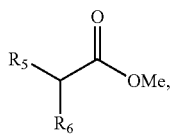

and reacting with A2 to give A4;

(2) reacting A3 and A4 with tosylmethyl isocyanide in the presence of NaH, tetrabutylammonium iodide, and dimethyl sulfoxide to obtain compound A5;

(3) reacting A5 with concentrated hydrochloric acid to obtain A6;

(4) conducting a hydrolysis reaction of A6 under alkaline conditions, and then acidulating with dilute hydrochloric acid to obtain A7;

(5) further reducing A7 with sodium borohydride to obtain A8;

(6) refluxing a toluene solution of A8 and the catalyst p-toluenesulfonic acid to obtain a compound A9 or A10;

wherein the definitions of $R_3$, $R_4$, $R_5$, $R_6$, n and m are the same as described in claim 1.

4. A method for preparing the fatty acid compound of formula II according to claim 1, wherein the method comprises the following steps:

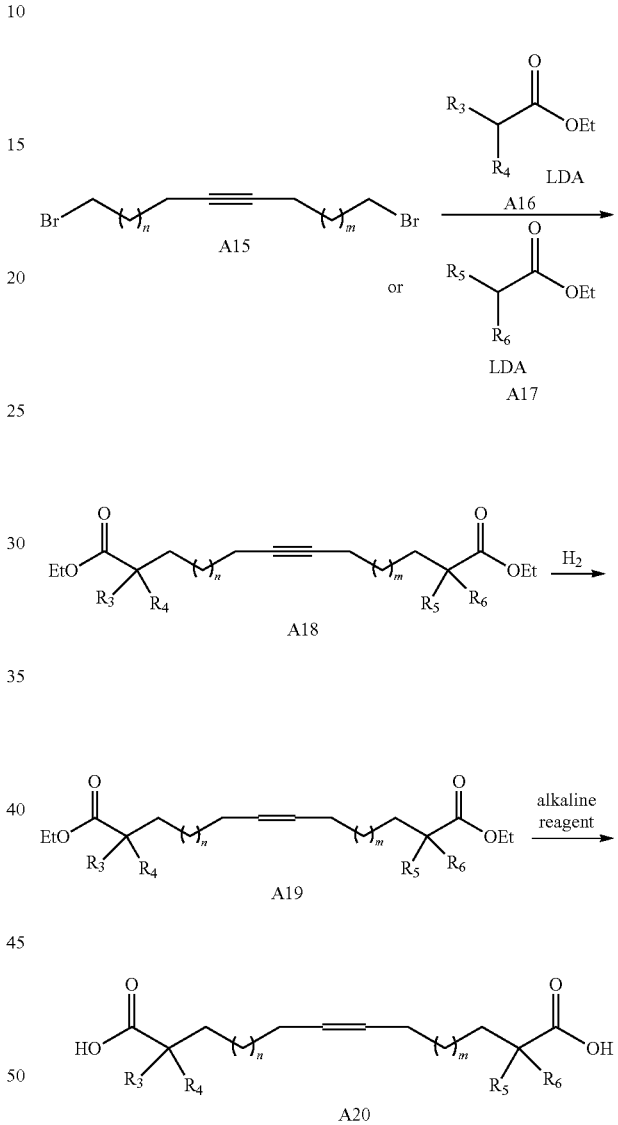

(1) condensing A15 with A16 or A17 in the presence of lithium diisopropylamide to obtain intermediate A18;

(2) conducting a hydrogenation reaction of A18 to obtain intermediate A19;

(3) conducting a hydrolysis reaction of A19 under alkaline conditions, and then acidulating with dilute hydrochloric acid to obtain A20;

wherein the definitions of $R_3$, $R_4$, $R_5$, $R_6$, n and m are the same as described in claim 1.

5. The method for preparing the fatty acid compound of formula II according to claim 4, wherein A15 is prepared using the following steps:

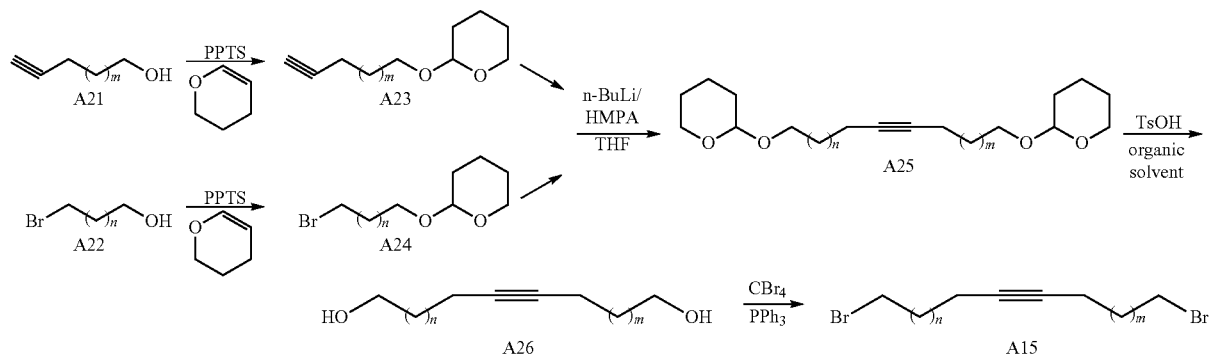

(1) reacting 1-alkynyl-alcohol compound A21 in the presence of pyridine p-toluenesulfonate and 2-tetrahydropyran to give intermediate A23; reacting 1-hydroxy-bromo compound A22 in the presence of pyridine p-toluenesulfonate and 2-tetrahydropyran to obtained intermediate A24;

(2) condensing A23 with A24 in the presence of n-butyllithium and HMPA to give intermediate A25;

(3) deprotection of A25 in the presence of p-toluenesulfonic acid and an organic solvent to obtain intermediate A26;

(4) reacting A26 with carbon tetrabromide and triphenylphosphine to give A15.

6. A method for preparing the fatty acid compound of formula II according to claim 1, wherein the method comprises the following steps:

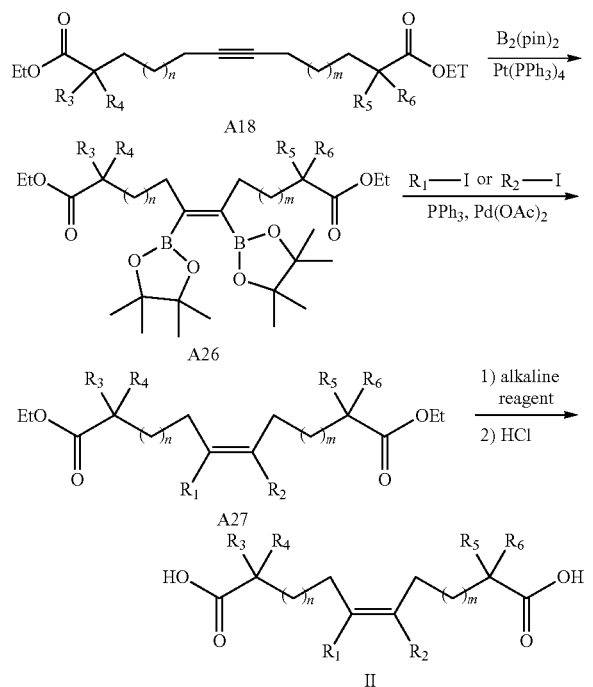

(1) reacting intermediate A18 with bis(pinacolato)diboron catalyzed by Tetrakis(triphenylphosphine)platinum to form intermediate A26;

(2) conducting a coupling reaction with A26 and iodide $R_1I$ or $R_2I$ to give intermediate A27;

(3) conducting a hydrolysis reaction of A27 under alkaline conditions, and then acidulating with dilute hydrochloric acid to obtain the compound represented by the formula II;

wherein, the definitions of $R_1$, $R_2$, $R_3$, $R_4$, $R_5$, $R_6$, m and n are the same as described in claim 1.

7. A method for treating obesity or diabetes, comprising the step of administering to a subject in need of such treatment an effective amount of the fatty acid compound or pharmaceutically acceptable salts thereof according to claim 1.

8. A pharmaceutical composition for treating obesity or diabetes, comprising:
one or more compounds selected from the group consisting of the fatty acid compound and pharmaceutically acceptable salts thereof according to claim 1 as an active ingredient; and
one or more pharmaceutically acceptable carrier.

9. The method for preparing the fatty acid compound of formula II according to claim 4, wherein A15 is prepared using the following steps:

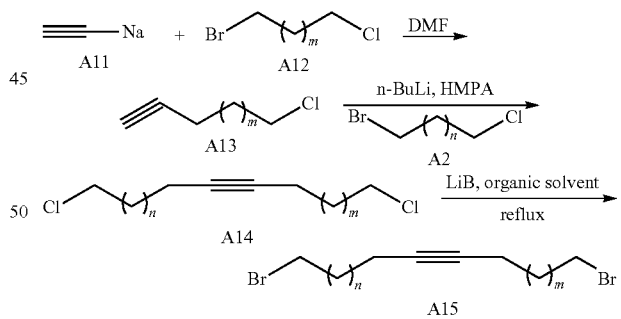

(1) reacting sodium acetylide A11 with bromo A12 in DMF to obtain intermediate A13;

(2) condensing alkynyl compound A13 and brominated compound A2 in the presence of n-butyl lithium and hexamethylphosphoric triamide to give intermediate A14;

(3) refluxing intermediate A14 with lithium bromide in an organic solvent to give A15.

* * * * *